(12) United States Patent  (10) Patent No.: US 9,381,361 B2
Giovangrandi et al.  (45) Date of Patent: Jul. 5, 2016

(54) CONTROL OF CARDIAC EXCITABILITY USING HIGH FREQUENCY SIGNALS

(71) Applicant: The Board of Trustees of the Leland Stanford Junior University, Palo Alto, CA (US)

(72) Inventors: Laurent Giovangrandi, Palo Alto, CA (US); Burak Dura, Cambridge, MA (US); Michael Q. Chen, Sunnyvale, CA (US); Omer T. Inan, Palo Alto, CA (US); Paul J. Wang, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 150 days.

(21) Appl. No.: 14/348,550

(22) PCT Filed: Oct. 4, 2012

(86) PCT No.: PCT/US2012/058602
§ 371 (c)(1),
(2) Date: Mar. 28, 2014

(87) PCT Pub. No.: WO2013/052574
PCT Pub. Date: Apr. 11, 2013

(65) Prior Publication Data
US 2014/0228837 A1  Aug. 14, 2014

Related U.S. Application Data

(60) Provisional application No. 61/543,103, filed on Oct. 4, 2011, provisional application No. 61/543,115, filed on Oct. 4, 2011, provisional application No. 61/543,125, filed on Oct. 4, 2011.

(51) Int. Cl.
*A61B 18/00* (2006.01)
*A61N 1/365* (2006.01)
(Continued)

(52) U.S. Cl.
CPC ............... *A61N 1/365* (2013.01); *A61B 18/14* (2013.01); *A61N 1/06* (2013.01); *A61N 1/3622* (2013.01);
(Continued)

(58) Field of Classification Search
CPC . A61N 1/365; A61N 1/3622; A61N 1/36114; A61N 1/36171; A61N 1/3627; A61B 18/14; A61B 2018/00351; A61B 2018/00577; A61B 2018/00642
See application file for complete search history.

(56) References Cited

U.S. PATENT DOCUMENTS 4,768,512 A  9/1988 Imran
5,450,846 A  9/1995 Goldreyer
(Continued)

FOREIGN PATENT DOCUMENTS

WO  97/04702 A1  2/1997
WO  2011/029029 A2  3/2011
WO  2013/052574  1/2013

OTHER PUBLICATIONS

EPO Supplementary Search Report, EP 12837819, May 7, 2015, 1 sheet.
(Continued)

*Primary Examiner* — Catherine Voorhees
(74) *Attorney, Agent, or Firm* — Crawford Maunu PLLC

(57) ABSTRACT

Certain embodiments of the present disclosure are directed toward devices, methods and systems for controlling depolarization in cardiac cells. One such device includes one or more circuits that are configured and arranged to generate an electrical stimulus at a high frequency. The circuit is configured to provide electrical stimulus over a period of time sufficient to depolarize the cardiac cells. An electrode arrangement is configured and arranged to deliver the high frequency electrical stimulus to cardiac cells and depolarize the cardiac cells.

24 Claims, 32 Drawing Sheets

(51) Int. Cl.
*A61N 1/362* (2006.01)
*A61N 1/36* (2006.01)
*A61B 18/14* (2006.01)
*A61N 1/06* (2006.01)

(52) U.S. Cl.
CPC ............. *A61B 2018/00351* (2013.01); *A61B 2018/00577* (2013.01); *A61B 2018/00642* (2013.01); *A61N 1/3627* (2013.01); *A61N 1/36114* (2013.01); *A61N 1/36171* (2013.01)

(56) References Cited

U.S. PATENT DOCUMENTS

| | | | |
|---|---|---|---|
| 6,431,173 | B1 | 8/2002 | Hoffmann |
| 6,754,535 | B2 * | 6/2004 | Noren ............ A61N 1/371 600/509 |
| 2003/0208239 | A1 | 11/2003 | Lu |
| 2007/0178579 | A1 | 8/2007 | Ross et al. |
| 2008/0208271 | A1 * | 8/2008 | Sih ............ A61N 1/05 607/5 |
| 2011/0152956 | A1 * | 6/2011 | Hincapie Ordonez ....... A61B 5/4041 607/4 |
| 2012/0215269 | A1 * | 8/2012 | Tandri ............. A61N 1/06 607/4 |

OTHER PUBLICATIONS

A. Nygren et al. "Mathematical model of an adult human atrial cell: The role of K+ currents in repolarization." Circ. Res., vol. 82, pp. 63-81 (1998).

H. Tandrie et al. "Reversible Cardiac Conduction Block and Defibrillation with High Frequency Electric Field." Sci. Transl. Med. 3(102), 15 pgs (Sep. 28, 2011).

B. Dura et al. "High-Frequency Electrical Stimulation of Cardiac Cells and Application to Artifact Reduction." Biomedical Engineering, 59(5), pp. 1381-1390 (May 2012). Filed as an Appendix in the underlying provisional application.

B. Dura et al. "Spatiotemporally Controlled Cardiac Conduction Block Using High-Frequency Electrical Stimulation." PLOS ONE, DOI: 10.1371/journal.pone.0036217, 9 pgs. (Apr. 30, 2012). Filed as an Appendix in the underlying provisional application.

* cited by examiner

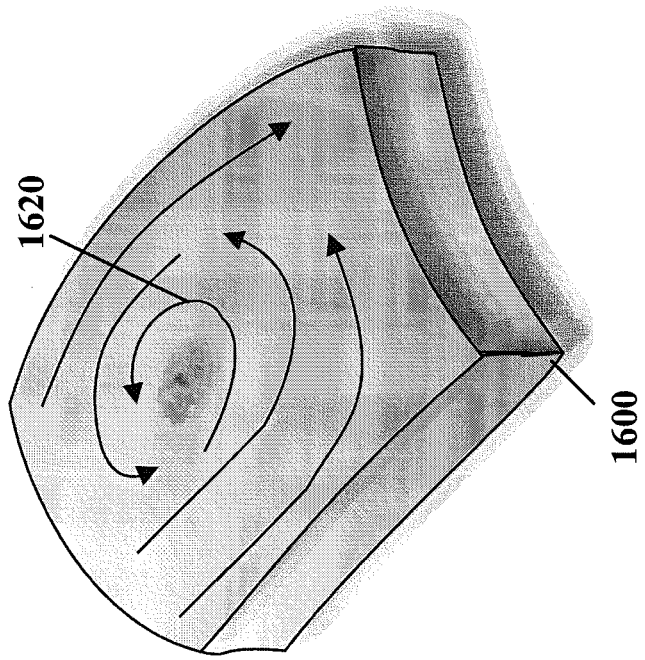
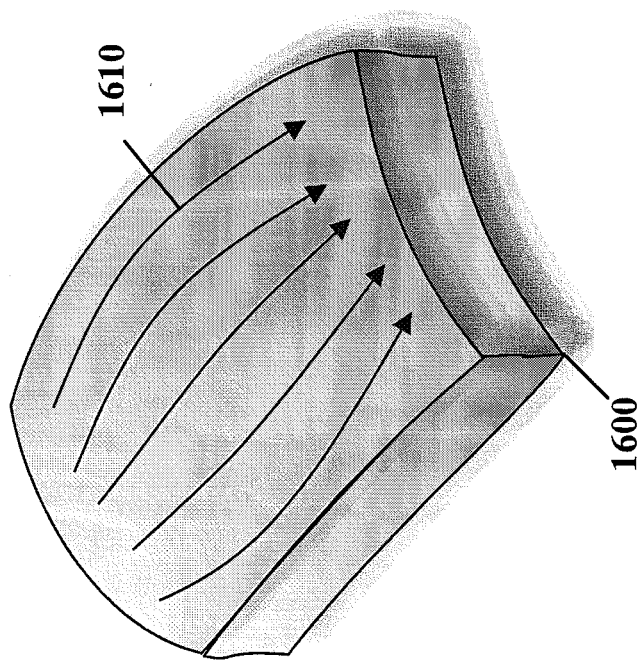
FIG. 16

FIG. 29A-C d
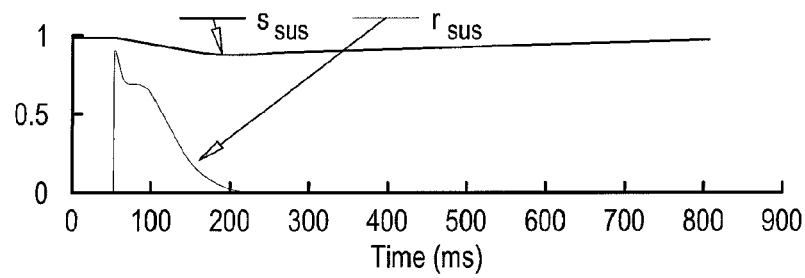

e
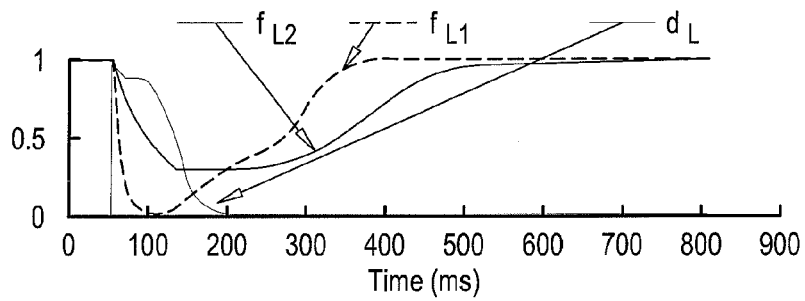

| m | :Activation gating variable for $Na^+$ channel |
| --- | --- |
| $h_1, h_2$ | :Fast and slow inactivation gating variables for $Na^+$ channel |
| $d_L$ | :Activation gating variable for $CA^{2+}$ channel |
| $f_{L1}, f_{L2}$ | :Fast and slow inactivation gating variables for $CA^{2+}$ channel |
| $r_{sus}$ | :Activation gating variable for $K^+$ channel |
| $s_{sus}$ | :Inactivation gating variable for $Na^+$ channel |

FIG. 29D-E

CONTROL OF CARDIAC EXCITABILITY USING HIGH FREQUENCY SIGNALS

OVERVIEW

Electrical stimulus of cardiac cells can be used in cardiac electrophysiology and for various therapies and treatments. Electrical inhibition of cardiac activity includes the ability to prevent cells from further generating an action potential. Pacing/capture of cardiac cells involves the generation of action potentials in the cardiac tissue. For example, pacing can be carried out using a small device (pacemaker) that is located in the chest or abdomen. This pacing can be used to help control abnormal heart rhythms by delivering electrical pulses to prompt the heart to beat at a normal rate.

Relating to pacing of the heart, are problems with the rate or rhythm of the heartbeat (arrhythmia). Arrhythmias can include heartbeats that are too fast (tachycardia), too slow (bradycardia), or irregular. Arrhythmias can adversely affect the heart's ability to pump blood to the body. Pacing of the heart (e.g., using a pacemaker) can be used as a treatment for arrhythmias. A pacemaker also can help a person who has abnormal heart rhythms resume a more active lifestyle.

A particular type of arrhythmia is a re-entry arrhythmia. In a re-entry arrhythmia, the cells of the heart can enter a repeating state of activity. The re-entry arrhythmia can be caused by damaged cells that create a re-entry path for a depolarization wave (activation of cardiac cells). Re-entry arrhythmias are therefore treated by destroying (ablating) cardiac cells in the re-entry pathway.

Electrical stimulus can also be used in vitro for a variety of different applications. Aspects of the present disclosure recognize that electrical stimulus of cardiac cells, whether in vivo or not, can be provided in a controllable and safe manner using high frequency stimulus.

SUMMARY

Various aspects of the present disclosure are directed to devices, methods and systems that utilize high frequency stimuli to depolarize cardiac cells, inhibit excitability through prolonged depolarization of cardiac cells with high frequency stimuli, and stimulate cardiac cells to create action potentials using high frequency stimuli.

Certain embodiments of the present disclosure are directed toward a device for controlling depolarization in cardiac cells. The device includes one or more circuits that are configured and arranged to generate an electrical stimulus at a frequency exceeding 1 kHz and less than 500 kHz. The circuit is configured to provide electrical stimulus over a period of time sufficient to depolarize the cardiac cells. An electrode arrangement is configured and arranged to deliver the high frequency electrical stimulus to cardiac cells and depolarize the cardiac cells.

Consistent with embodiments, a method is used to inhibit excitability of cardiac cells. A high frequency electrical stimulus is generated at a frequency exceeding 1 kHz and less than 500 kHz. The high frequency electrical stimulus is delivered to the cardiac cells. The high frequency electrical stimulus is delivered to the cardiac cells over a period of time sufficient to inhibit further action potentials in the cardiac cells.

Various embodiments are directed toward methods for modeling cardiac dysfunctions, such as re-entry arrhythmia A propagating depolarization wave can be generated in cardiac tissue by providing an electrical stimulus at a first location in the cardiac tissue. The propagation of the depolarization wave is then directed back to the first location by inhibiting depolarization of cardiac tissue using high frequency electrical stimulus applied to portions of the cardiac tissue and thereby creating a re-entry arrhythmia.

Certain embodiments are directed toward methods for creating depolarization in cardiac cells. The methods can include the generation of a high frequency electrical stimulus at a frequency exceeding 1 kHz and less than 500 kHz. The high frequency electrical stimulus is delivered to the cardiac cells. An electrical signal is then received from the cardiac cells and high frequency components are filtered from the received electrical signal. A depolarization event is detected using the filtered electrical signal. In response to detecting the depolarization event, the delivery of the high frequency electrical stimulus to the cardiac cells is stopped.

The above discussion is not intended to describe each embodiment or every implementation of the present disclosure. The figures, detailed description, and claims that follow more particularly exemplify various embodiments.

BRIEF DESCRIPTION OF THE DRAWINGS

Aspects of the present disclosure may be more completely understood in consideration of the detailed description of various embodiments of the present disclosure that follows in connection with the accompanying drawings, in which:

FIG. 16 shows an example human heart tissue sections with (left) homogenous tissue and homogeneous depolarization, and (right) inhomogeneous tissue and electrical signal re-entry, consistent with various aspects of the present disclosure;

Figure 1:
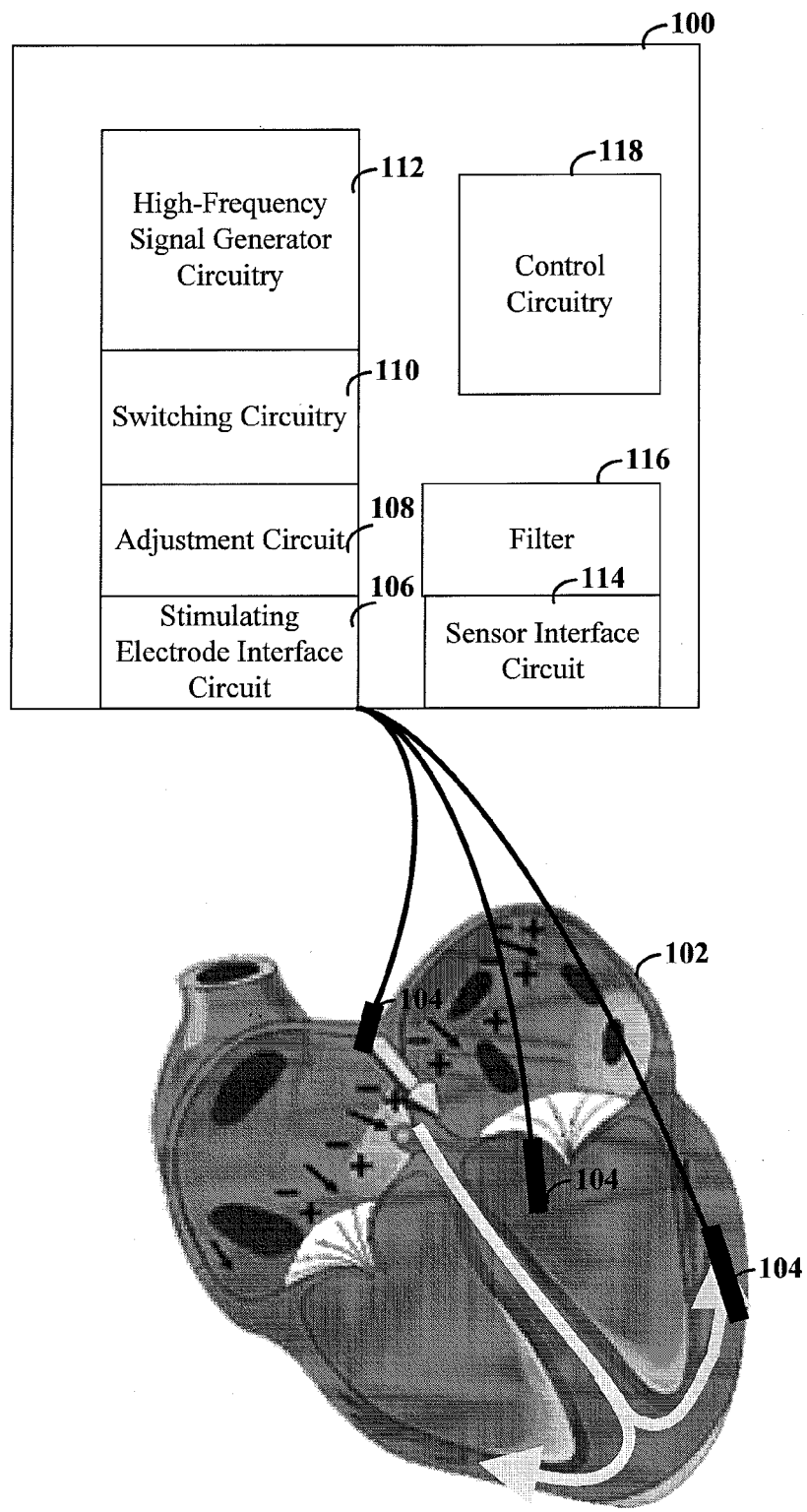
FIG. 1 shows a block diagram for a system configured to deliver high frequency electrical stimulation to cardiac tissue, consistent with various aspects of the present disclosure.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the scope of the disclosure including aspects defined in the claims.

DETAILED DESCRIPTION

The present disclosure relates to using high frequency stimulation to inhibit action potentials in target cardiac cells. Particular embodiments are directed toward applying an electrical stimulus in the form of a biphasic waveform that alternates voltages at high frequencies and is continuously applied to generate and/or inhibit action potentials in the target cardiac cells. While the present disclosure is not necessarily limited to such devices and applications, various aspects of the disclosure may be appreciated through a discussion of examples using these and other contexts.

Embodiments of the present disclosure are directed toward the use of high frequency electrical waveforms to produce an action potential by depolarization of cardiac tissue. More particular embodiments stem from the recognition that such stimulus, by way of high frequency waveforms, can be used in connection with a variety of different applications, devices and systems.

Consistent with certain embodiments, high frequency electrical stimulus can be applied to cardiac tissue with power (current and/or voltage controlled) and duration that is sufficient to depolarize the cardiac tissue and cause a corresponding action potential to occur. In particular embodiments, the high frequency electrical stimulus can then be ceased. Thereafter, additional sufficient high frequency electrical stimulus can be applied to create subsequent action potentials, as desired. This allows for action potentials to be selectively initiated and controlled.

In other embodiments, the high frequency stimulus can be maintained after depolarization to inhibit further depolarization events, e.g., by extending the depolarization of an action potential until the stimulus is terminated. This surprising result was obtained by careful selection of the stimulus parameters, which can include current and/or voltage level. The stimulus level necessary to cause depolarization is sometimes referred to as the threshold level. Sub-threshold stimulus can be used to discourage action potentials; however, such stimulus is often limited to timing the stimulus synchronously with an action potential that is to be discouraged. Particular embodiments recognize that high frequency stimulus allows for the use of supra-threshold stimulus levels. This can be particularly useful for inhibiting using stimulation that is not synchronized with the action potential(s).

Particular embodiments using high frequency stimulus to inhibit recognize that the inhibition can be localized. For instance, the stimulus can inhibit action potentials in specific areas in contact with, or near to, a stimulus electrode. This special precision can be particularly useful for a number of applications including, but not limited to, ablation guidance, disease modeling and other uses of targeted inhibition. Moreover, certain embodiments are based upon the recognition that cardiac tissue that is inhibited using high frequency can resume normal pacing/action potentials shortly after the stimulus is removed. This temporal precision can also be particularly useful for a number of different applications.

Still other embodiments relate to pacing of cardiac tissue using high frequency stimulus. This pacing can use supra-threshold stimulus levels to cause one or more action potentials in the cardiac tissue. By alternating the application and removal (or reduced stimulus level) of the applied stimulus, a sequence of individual action potentials, or pulse train, can be generated.

Consistent with embodiments of the present disclosure, action potentials can be inhibited in excitable cells (cardiac cells) using high frequency electrical signals as stimuli. Particular embodiments are directed toward applying an electrical stimulus in the form of a biphasic waveform that alternates voltages at high frequencies and is continuously applied to inhibit action potentials in the target cells. It has been discovered that the use of high frequency waveforms can reduce undesirable generation of action potentials in cells. For specific stimulus frequencies, action potentials are inhibited when the signal amplitude is above a threshold and undesired action potentials are not generated when the signal amplitude is below the threshold. This can be particularly useful for reducing or eliminating unwanted generation of action potentials, e.g., as may be the result of the effective signal amplitude being reduced with respect to the distance from the signal source.

Certain embodiments of the present disclosure are directed toward measuring electrical activity (action potentials) of excitable cells using a sensor located proximate to an electrode that delivers a stimulus to the excitable cells. Electrical signals from the stimulating waveform can be filtered out using frequency-based filtering. For instance, the relatively-high and stable frequency of the stimulus allows for a band-pass filter to effectively remove the stimulus. This filtering can be effective enough to allow for an action potential (or absence thereof) to be measured at the same time that the stimulus is being applied. In certain implementations, a single electrode can be used both for delivery of the stimulus and for measurement of the electrical activity of the excitable cells.

Aspects of the present disclosure are directed toward a stimulus waveform provided at a frequency of between 0.5 kHz and 10 kHz. More particular embodiments are directed towards frequencies of between 2.5 kHz and 5 kHz for cardiac cells. Various embodiments recognize that the particular frequency can be selected according to parameters that can include, but are not limited to, power, amplitude, and the ability to decouple the stimulus from action potentials for sensing purposes.

Experimental results suggest that excitable cells rectify membrane currents in response to high frequency, externally-applied stimulus. The present disclosure recognizes that a biphasic waveform can therefore provide an effective stimulus voltage that is more than the absolute voltage amplitude with respect to the common/resting voltage of the cell environment. The use of a biphasic waveform can also allow the use of a stimulus source that uses switching circuitry to generate the biphasic waveform from an absolute voltage less than the voltage swing from the negative voltage to the positive voltage (e.g., by reversing the polarity of the stimulating electrodes relative to the generated voltage). Accordingly, the stimulus waveforms can be biphasic in certain embodiments; however, the stimulus waveform can also be monophasic in certain other embodiments.

Various embodiments of the present disclosure recognize that a closed-looped stimulus system can be implemented by filtering out the stimulus from a sensed signal. The filtered signal can be used as a feedback to control the stimulus. For instance, the stimulus amplitude can be adjusted in response to whether or not a successful capture of myocardium is sensed. Other parameters that can be adjusted include, but are not limited to, the stimulus duration and frequency.

Various embodiments of the present disclosure are directed toward inhibiting excitation of portions of cardiac tissue for use with in vitro applications. One such application relates to modeling abnormalities of cardiac tissue. This modeling can be used for various purposes including, but not limited to, drug screening and/or disease modeling. For instance, a portion of cardiac tissue can be inhibited to mimic damaged/scarred tissue. The high frequency stimulus can be particularly useful for enabling, disabling and modifying the modeled damaged/scarred tissue (e.g., as opposed to permanently damaging the tissue). Particular embodiments may include the modeling of re-entry pathways that can cause sustained loops of depolarization.

Various embodiments of the present disclosure are directed toward inhibiting excitation of portions of cardiac tissue for use with in vivo applications. One such application relates to radio-frequency (RF) ablation. RF ablation can be used to ablate dysfunctional cells using heat generated from the high frequency alternating current to treat a medical disorder. In cardiac applications it can be difficult to properly locate the dysfunctional cells, leading to ablation of healthy cells by mistake.

In order to assess the proper location for ablation, aspects of the present disclosure inhibit cardiac cells using high frequency electrical stimulus. The inhibition of the cardiac cells mimics the (permanent) effect of ablation of the same cells. In this manner, the effectiveness of the inhibition on treating the abnormality can be assessed while the cardiac cells are inhibited. Such procedures can be further assisted by directly sensing the activity of the cardiac cells while the high frequency, electrical stimulus is being applied. This can, among other things, verify that the inhibition is effective.

Various embodiments of the present disclosure are directed toward inhibiting cardiac cells to treat fibrillation. The use of high frequency, electrical stimulus allows for the inhibition of the cardiac cells in response to a detected fibrillation. Multiple lead electrodes, mesh electrodes, sock electrodes, balloon electrodes or other stimulus delivery devices can be used to increase the effective area of the inhibition.

Various embodiments of the present disclosure recognize that a closed-looped stimulus system can be implemented by filtering out the stimulus from a sensed signal. The filtered signal can be used as a feedback to control the stimulus. For instance, the stimulus amplitude can be adjusted in response to whether or not a successful capture of myocardium is sensed. Other parameters that can be adjusted include, but are not limited to, the stimulus duration and frequency. One such embodiment provides stimulus until a capture is detected and then stops the stimulus. The closed feedback loop allows for a myriad of different configurations and settings. For instance, if a capture is not detected after the stimulus has been present for a set/maximum duration, then the amplitude of the stimulus can be increased. This can be useful for compensating for changes in the capture threshold (e.g., due to desensitization of the cells, corrosion of the stimulus electrode and/or movement of the stimulus electrode).

Certain aspects of the present disclosure are directed toward the recognition that high frequency pacing can facilitate the simultaneous detection of action potentials using sensing electrodes. Action potentials in cells have a low signal strength that can be difficult to accurately measure and detect. Often an externally applied stimulus (whether to pace or inhibit) can drown this low signal strength making the detection of action potentials difficult or even impossible. Accordingly, aspects of the present disclosure can take advantage of the frequency separation between the characteristics of an action potential and those of an applied high frequency stimulus. Specialized filters, amplifiers and signal conditioning circuits can be used to detect action potentials while reducing interference from the high frequency stimulus.

Various embodiments can use the detection of action potentials and/or other inputs as a feedback to control an applied stimulus. For instance, control over high frequency stimulation used to inhibit can be responsive to detection of action potentials or their absence. This can include, for example, determining a stimulus level by gradually increasing the stimulus strength until action potentials are no longer detected or gradually decreasing the stimulus strength until an action potential is detected. The determined stimulus level can then be used to set the stimulus strength for subsequent inhibition. Moreover, such adjustments can be ongoing and thereby account for dynamic changes in the cardiac system being inhibited. This type of closed loop feedback can be useful for many different applications.

In other instances, a stimulus level can be determined for a desired pacing application. Subsequent pacing stimulus bursts (e.g., where the burst applies a high frequency signal for the duration of the burst) can thereafter be set to a level based upon this determination. Moreover, the length of the pacing bursts can be adjusted based upon the detection of an action potential. In particular, a pacing burst can apply a high frequency stimulus and the pacing burst can be ceased in response to the detection of an action potential.

Certain embodiments are directed to the use of high frequency stimulus to guide ablation of cardiac tissue. Ablation of cardiac tissue can be used to treat dysfunctional tissue, such as dysfunctional tissue causing re-entry arrhythmias. Ablation of tissue is generally non-reversible and can carry significant risks. Aspects of the present disclosure recognize that tissue targeted for ablation can be first inhibited by high frequency stimulus in order to assess the effectiveness of ablation at the stimulus location. For instance, ablation for re-entry arrhythmias causes the ablated tissue to cease electrical activity (action potentials) and therefore inhibition by high frequency stimulation can be used as a reasonable approximation of ablation.

Various embodiments are directed toward the selective use of inhibition to treat cardiac dysfunction. For instance, inhibition can be applied in response to detecting the onset of a particular dysfunction, such as fibrillation or an arrhythmia. This can be particularly useful for treatment of chronic cardiac dysfunction (e.g., separate from permanent ablation or high power defibrillators). The inhibition can be applied on an as-needed basis and thereby allow the heart to function (near) normally until and unless there is a particular need for inhibition treatment.

Other aspects of the present disclosure are directed toward the use of both pacing and inhibition in the same system. For instance, pacing could be applied in a first location while inhibition is applied in a second location. This dual function can be particularly useful due to the temporal and spatial precision that can be achieved using high frequency stimulation. For instance, pacing could be provided at a first location, while inhibition could be provided at a second location in response to detection of an arrhythmia.

Alternatively, inhibition could be provided at a first point in the conduction pathway of the heart. At a subsequent point, pacing could be provided. This could be particularly useful for bypassing conduction blocks, as may be present in cardiac dysfunctions such as left bundle branch blocks (LBBB). For instance, this inhibition/pacing combination could be applied at, near or surrounding the bundle of His. Moreover, the ability to simultaneously detect depolarization in the vicinity of applied stimulus can allow for the detection of an incoming depolarization/pacing signal near the point of inhibition. This can then be used to trigger subsequent pacing and allow for the heart's intrinsic pacing rate to be maintained.

Turning now to the figures, FIG. 1 depicts a block diagram for a system configured to deliver high frequency electrical stimulation to cardiac tissue. Device 100, including control circuitry 118, is configured and arranged to provide the high frequency electrical stimulation to targeted cardiac cells 102, which can be located in vivo or in vitro. FIG. 1 depicts the targeted cardiac cells 102 as being part of a fully functioning heart; however, various embodiments contemplate other applications. For instance, cardiac cell cultures can form the targeted cardiac cells 102.

One or more electrodes 104 can be used to deliver the high frequency electrical stimulation to the targeted cardiac cells 102. Device 100 can facilitate this delivery using one or more stimulating electrode interface circuits 106. In certain instances, the interface circuit 106 can include a signal amplifier circuit, a signal driver circuit and/or a digital-to-analog converter (DAC) circuit. This interface circuit 106 can thereby be designed to provide adequate power while maintaining the signal integrity at high frequencies.

Consistent with certain embodiments, parameters for the high frequency electrical stimulation can be adjusted by way of adjustment circuitry 108. For instance, the current of the provided stimulus can be increased or decreased by way of adjustment circuitry 108. In another instance, the amplitude of the provided stimulus can be increased or decreased. Depending upon the design of the interface circuit 106, such adjustments could be carried out by modifying the gain of an associated amplifier.

Embodiments of the present disclosure can also use switching circuitry 110. For instance, switching circuitry 110 can be used to enable or disable the provided stimulus. Switching circuitry 110 could also be used to provide (or not provide) the high frequency stimulus to specific electrodes 104. Yet another possibility includes the use of switching circuitry 110 to route high frequency stimuli with different properties (e.g., frequencies, voltages, current levels or duty cycles) to different ones of electrodes 104.

High frequency signal generator circuitry 112 can be configured to generate a high frequency signal. For instance, the generate signal can be a biphasic square wave having a frequency between 1 kHz and 50 kHz. Moreover, even higher frequencies are also believed to be useful including, but not necessarily limited to frequencies up to at least 500 kHz. Other possibilities include, but are not necessarily limited to, modified frequency ranges, sawtooth waves, sine waves and triangle waves. These and other modifications can also be used to reduce artifacts, relative to detection of action potentials and caused by the high frequency stimulus.

Certain embodiments of the present disclosure also contemplate a signal receive/detection path from the cardiac cells 102. This can allow for a feedback loop that can be used to modify the parameters for the high frequency stimulus. A sensor interface circuit 114 can receive electrical signals from various sources including, but not necessarily limited to, one or more of electrodes 104. Sensor interface circuit 114 can include signal conditioning circuits and/or an analog-to-digital converter (ADC) circuit.

Various embodiments are directed toward a filter circuit 116. This filter circuit can be configured to filter out the high frequency stimulus, while allowing the detection of action potentials.

Figure 2:
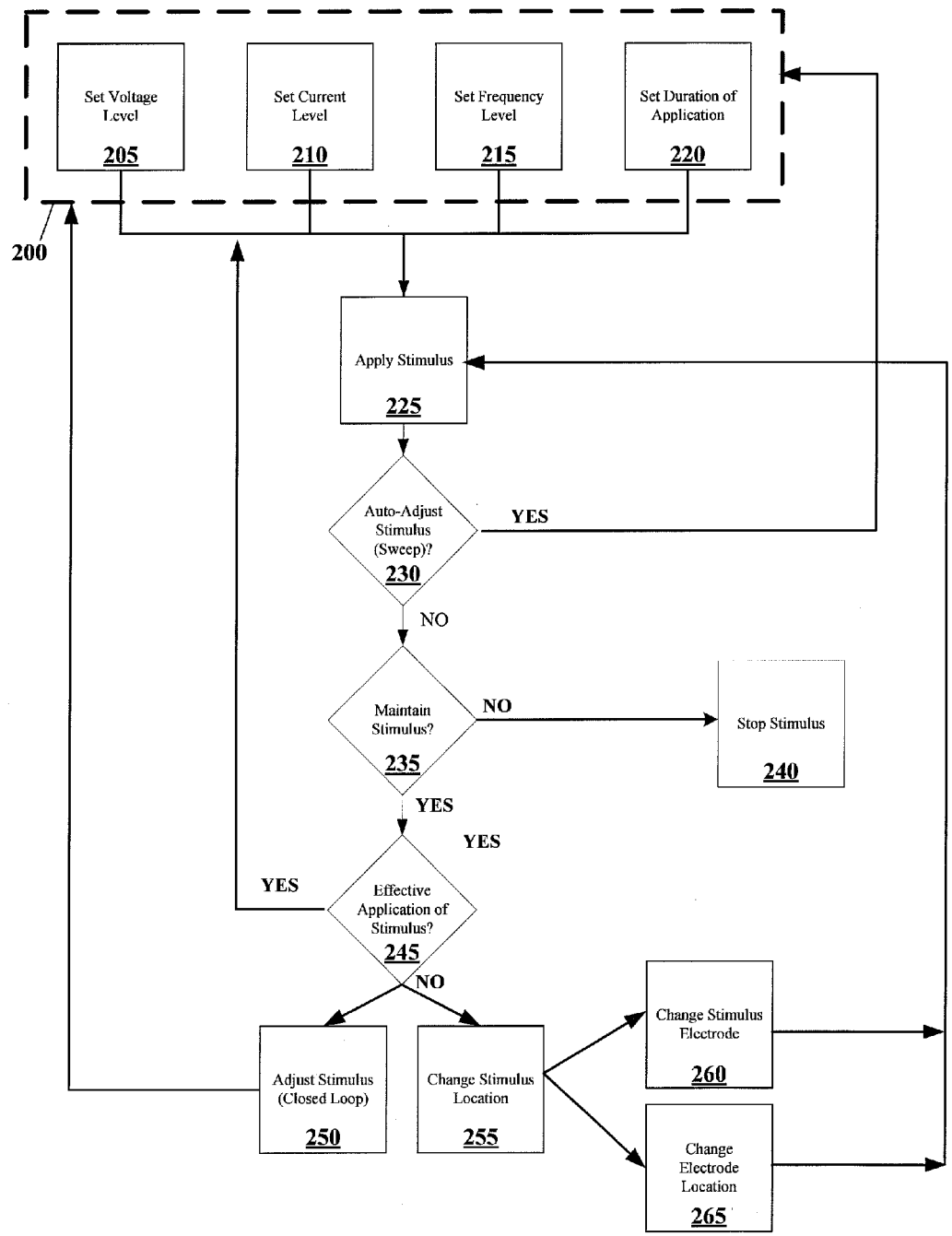
FIG. 2 shows an example flow diagram, consistent with various aspects of the present disclosure.

FIG. 2 depicts an example flow diagram, consistent with various aspects of the present disclosure. As shown in block 200, aspects of the present disclosure utilize a number of different parameters for applying a stimulus. The stimulus is set, as non-limiting examples, by selecting appropriate values for one or more of: a voltage level 205; a current level 210; a frequency level 215; and the duration for which the stimulus is applied 220. Other parameters are also possible.

Once the parameters have been set, a stimulus can then be applied to the targeted cardiac cells, as illustrated in block 225. In certain embodiments, a range of the various parameters can be swept and applied as a stimulus. In this manner, the reaction of the targeted cardiac cells can be observed in response to the range of stimuli applied. Subsequently, in certain embodiments, a predetermined value of the parameters is selected based upon the ranges of the parameters applied.

In certain embodiments, and as illustrated in block 230, the stimulus can be adjusted as part of an automatic adjustment. The adjustment of the stimulus can be based upon a sweep through available stimulation parameters. Data could be collected regarding the effectiveness of the stimulus and correlated to the various sweep values. A desired parameter setting could then be selected and used. In certain embodiments of the present disclosure, where a stimulus is presented to pace the cardiac tissue, the stimulus could be adjusted based on the ability to consistently capture the cardiac tissue. Additionally, a stimulus used to inhibit action potentials in the cardiac cells and subsequent to the depolarization would be adjusted depending upon whether or not the action potentials are not inhibited.

When the stimulus is adjusted, one or more of the parameters shown in block 200 are varied to produce the desired effect. In response to detecting an adequate response of the cardiac tissue, the system can maintain the stimulus according to selected values for the parameters. As shown in block 235, the stimulus can be stopped (240) at any point. This could occur, for instance, after an arrhythmia or fibrillation has been terminated. Certain aspects relate to determining the effectiveness of the stimulus, as shown in block 245. In certain embodiments, the stimulus would be desired for a limited amount of time (e.g., limited depolarization of heart tissue). In other embodiments, the application of the stimulus is desired over a longer period of time, as would be necessary for blocking propagation of an electrical wave through cardiac tissue. The effectiveness of the stimulus depends on the application for which it is used. For example, if the stimulus is used to generate one or more action potentials (e.g., for pacing), the stimulus will not be determined as being effective unless an action potential is propagated. Further, if the stimulus is used for inhibiting action potentials, the effectiveness of the inhibition can be measured by detecting the presence or absence of action potentials, and the stimulus is adjusted as needed. Moreover, if the stimulus is used to terminate re-entry (as would occur in arrhythmia), the effectiveness of the stimulus would be determined based on whether or not a normal propagation of an electrical signal through the heart tissue occurs.

The determination of whether the stimulus application is effective can be used as part of a feedback loop for adjusting the stimulus, and therefore can help to optimize the applied stimulus. If the stimulus is not effective, the stimulus can be adjusted, as illustrated by the block 250 and/or the location of the applied stimulus can be changed, as illustrated by block 255. The stimulus location can be altered in a number of ways. For example, and as illustrated in block 260, the system can have multiple available electrodes and stimulus can be adjusted by selecting a different stimulus electrode. Depending upon the probe, the selection of different electrodes can correspond to stimulating at a new location, changing the amount of tissue that is affected by the stimulus by selecting an electrode with a different size, a different electrode shape or other variations.

Various embodiments of the present disclosure include multiple electrodes for applying a stimulus. The multiple electrodes can be implemented in an array, for example, and one or more of these electrodes are used for stimulating a targeted area. Various ones of the electrodes in the array are switched on or off. Additionally, the electrode(s) location can be changed, as illustrated in block 265. In certain embodiments, the location of the electrode is changed by moving the electrode to a new area within the targeted area in order to better provide a stimulus. In each instance of changing the waveform of the stimulus, changing the stimulus location, and adjusting the stimulus, the effectiveness of the stimulus will be determined again, as shown by the multiple feedback loops. This process allows for the proper application of a stimulus as used in various embodiments of the present disclosure. Moreover, some embodiments contemplate providing the stimulus to different electrodes at different times. This can be useful for a number of applications, including but not limited to, steering, facilitating or inhibiting the propagation of a depolarization wave.

Figure 3:
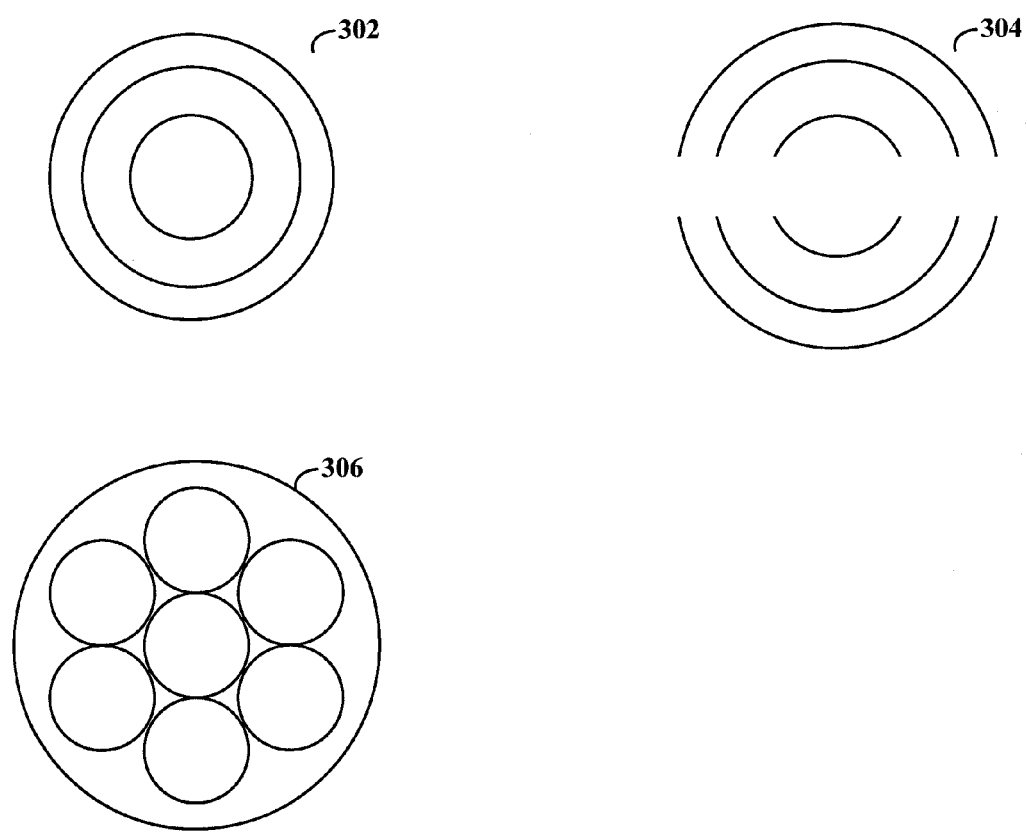
FIG. 3 shows several example configurations for electrodes, consistent with embodiments of the present disclosure.

FIG. 3 depicts several configurations for electrodes, consistent with embodiments of the present disclosure. There are a number of different therapeutic uses for high frequency stimulation, and accordingly, there exist many different configurations for electrodes that deliver such high frequency stimulation. For instance, electrode configuration 302 includes a number of concentric electrodes. This configuration can be particularly useful for adjusting the effective area over which the high frequency stimulation is applied. In certain uses, it may be beneficial to keep the effective area as small as possible, while still providing the desired benefit. Thus, consecutively smaller electrodes can be used to determine the smallest electrode that is usable for the particular benefit. A particular example relates to ablation. It can be desirable not to ablate more tissue than necessary. Accordingly, the required amount of tissue that should be ablated can be determined by testing the effectiveness of inhibition at different electrodes and then using the determined electrode to deliver the ablation energy. In another example, an outer ring can be used to inhibit, while an inner ring can be used to sense for action potentials. This can be particularly useful for determining whether or not the inhibition is effective.

Electrode configuration 304 includes a number of concentric half-circles. This type of configuration can be useful for controlling the direction of an initial depolarization wave. For instance, an inner electrode can be used to pace the cardiac tissue, while an outer, surrounding electrode can be used to inhibit the cardiac tissue. In this manner, the resulting depolarization wave is (at least initially) directed in a particular direction.

Electrode configuration 306 includes a large outer electrode that surrounds a number of smaller electrodes. A particular use of this electrode configuration relates to ablation mapping. In order to find the correct location for ablation, the outer/larger electrode can be used to inhibit while mapping for the correct location to ablate. Once the desired effect is achieved (e.g., termination of a re-entry arrhythmia), each of the smaller electrodes can be used to inhibit, and thereby, more precisely find a location to ablate.

Consistent with these and other embodiments, maintaining a suprathreshold stimulus (stimulus of amplitude large enough to initiate an action potential) over an extended period of time can result in a corresponding extension of the duration of depolarization (resulting from an action potential) and thereby can be used to inhibit further action potentials. Moreover, low-frequency pulse trains can lead to entrainment (repeated stimulation of action potentials), which can lead to the induction of fibrillation, and even hemodynamic collapse in vivo.

The stimulation with bursts of higher frequency biphasic (AC) (square) pulses has been shown to excite cardiac tissue, similarly to lower frequencies of stimuli. These bursts, if maintained for longer than the action potential duration, have been shown to extend the action potential until the stimulus is terminated. Without being limited by theory, computer simulations suggest that this inhibition is due to an ion channel mechanisms: the prolonged depolarization is the result of the counteracting of the outward $K^+$ repolarization current by the inward $Ca^{2+}$ current—sustained for the duration of the stimuli—while the suppression of further depolarization might be related to the inactivated $Na^+$ channels.

Various aspects of the present disclosure are directed toward a device for inhibiting excitability in cardiac cells. These devices include, for example, circuitry that generates an electrical stimulus at a frequency exceeding 1 kHz and less than 50 kHz. Additionally, the circuitry maintains the electrical stimulus over a period of time sufficient to inhibit action potentials in the cardiac cells. Devices for inhibiting excitability in cardiac cells, consistent with various aspects of the present disclosure, also include an electrode arrangement that delivers the high frequency electrical stimulus to cardiac cells and thereby inhibit action potentials in the cardiac cells.

In certain embodiments of devices for inhibiting excitability in cardiac cells, the high frequency electrical stimulus is between 2 kHz and 10 kHz. Moreover, in various embodiments, the high frequency electrical stimulus is a biphasic signal. Additionally, certain embodiments of the circuitry, included in devices of the present disclosure for inhibiting excitability in cardiac cells, are configured to filter the high frequency components from an electrical signal received from the cardiac cells and to monitor for action potentials in the filter electrical signal. Moreover, the electrode arrangement can be a single electrode that both provides the high frequency electrical stimulus and receives the electrical signals from the cardiac cells. Other embodiments of the electrode arrangement include a plurality of electrodes.

Aspects of the instant disclosure are also directed toward methods for inhibiting excitability of cardiac cells by generating a high frequency electrical stimulus at a frequency exceeding 1 kHz and less than 50 kHz. Further, these methods operate by delivering the high frequency electrical stimulus to the cardiac cells, and maintaining the high frequency electrical stimulus to the cardiac cells over a period of time sufficient to inhibit action potentials in the cardiac cells.

Certain more specific embodiments of methods, of the present disclosure, utilize a high frequency electrical stimulus that is between 2 kHz and 10 kHz. Other ranges include, but are not limited to 2 kHz to 5 kHz, 1 kHz to 10 kHz, 10 kHz to 50 kHz, 1 kHz to 25 kHz and 2 kHz to 25 kHz. In various embodiments, methods will include additional steps of receiving electrical signals from the cardiac cells, filtering high frequency components from the electrical signals, and detecting, from the filtered electrical signals, electrical action potentials of the cardiac cells. Additionally, in other embodiments, the high frequency stimulus is adjusted in real-time based on the electrical response of the cardiac cells.

Inhibition of electrical activity and more precisely inhibition of further depolarization (and associated conduction of depolarization) is possible in both cardiac and neuronal tissue. Blocking the propagation of action potentials down neuronal axons can be accomplished using trains of pulses, at various amplitudes and frequency. For cardiac tissue, a technique called subthreshold stimulation (STS) can be utilized, which has the ability to extend the action potential plateau phase, effectively blocking further depolarization. Subthreshold stimulation refers to stimuli with amplitude too low to initiate an action potential. However, when applied during the plateau phase of the action potential, they can extend this phase. Because this phase is refractory, the tissue held in this state cannot depolarize again. STS can have a low operational margin due to the requirement of subthreshold. Too low and the stimulus has no effect, too high and entrainment (stimulation of new action potentials) becomes a risk. This constraint precludes the use of the high-amplitude stimuli to capture large volume of cells/tissue. If timing is not precisely controlled, the STS may not be initiated during the plateau (diastolic) phase and is likely to be ineffective.

Figure 4:
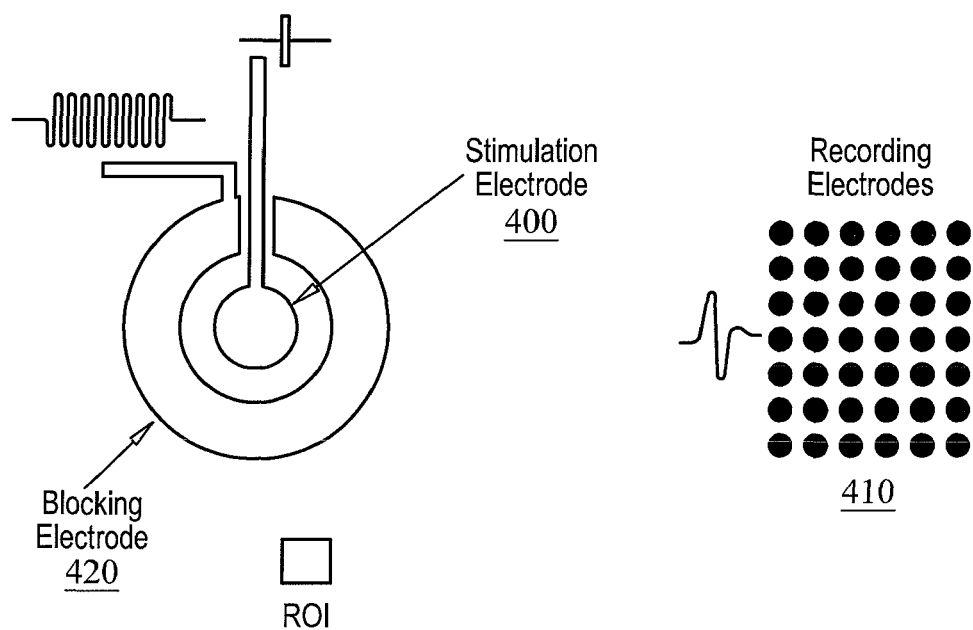
FIG. 4 shows an example arrangement of a stimulation electrode, blocking electrode and recording electrodes, consistent with various aspects of the present disclosure.
Figure 5:
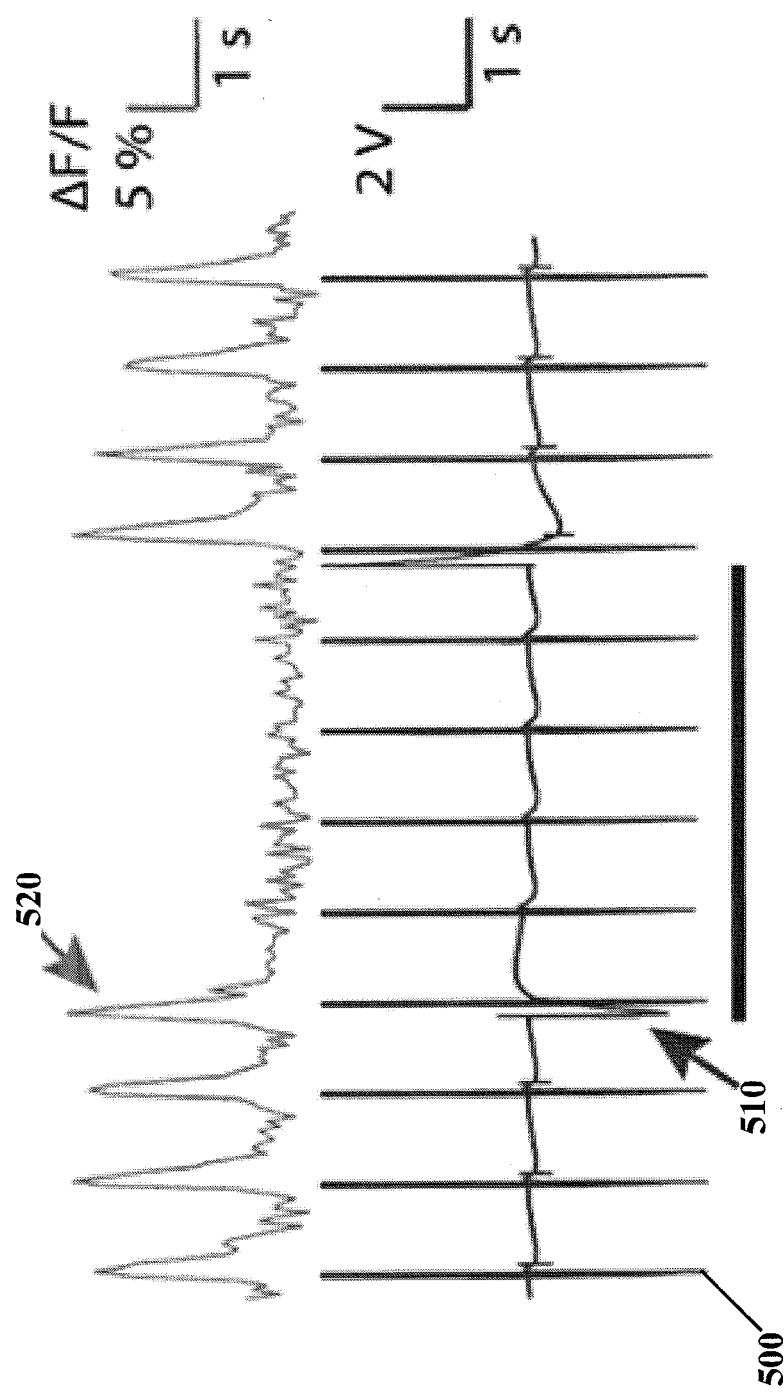
FIG. 5 shows an example demonstration of inhibition of depolarization by blockage of propagation of action potentials generated on a stimulation electrode, consistent with various aspects of the present disclosure.

FIG. 4 shows an example arrangement of electrodes demonstrating in vitro inhibition by preventing action potentials, consistent with embodiments of the present disclosure. FIG. 5 shows an example demonstration of inhibition of depolarization by blockage of propagation of action potentials generated on a stimulation electrode, consistent with various aspects of the present disclosure. In FIG. 5, the large spikes 500 in the lower trace are stimulation artifacts, and the small spikes 510 are APs. The upper traces 520 show intracellular calcium recording (control). The stimulation electrode 400 can generate action potentials that will propagate to the recording electrodes 410. A ring electrode 420 is used as a blocking electrode. The inhibition stimulus is applied to the ring electrode 420 (bar in FIG. 5) and triggers an early depolarization. This inhibits any further action potentials until the stimulus is removed. To avoid the onset response (an initial action potential), the stimulus can be timed to occur within the refractory period (similar to subthreshold stimulation).

Figure 6:
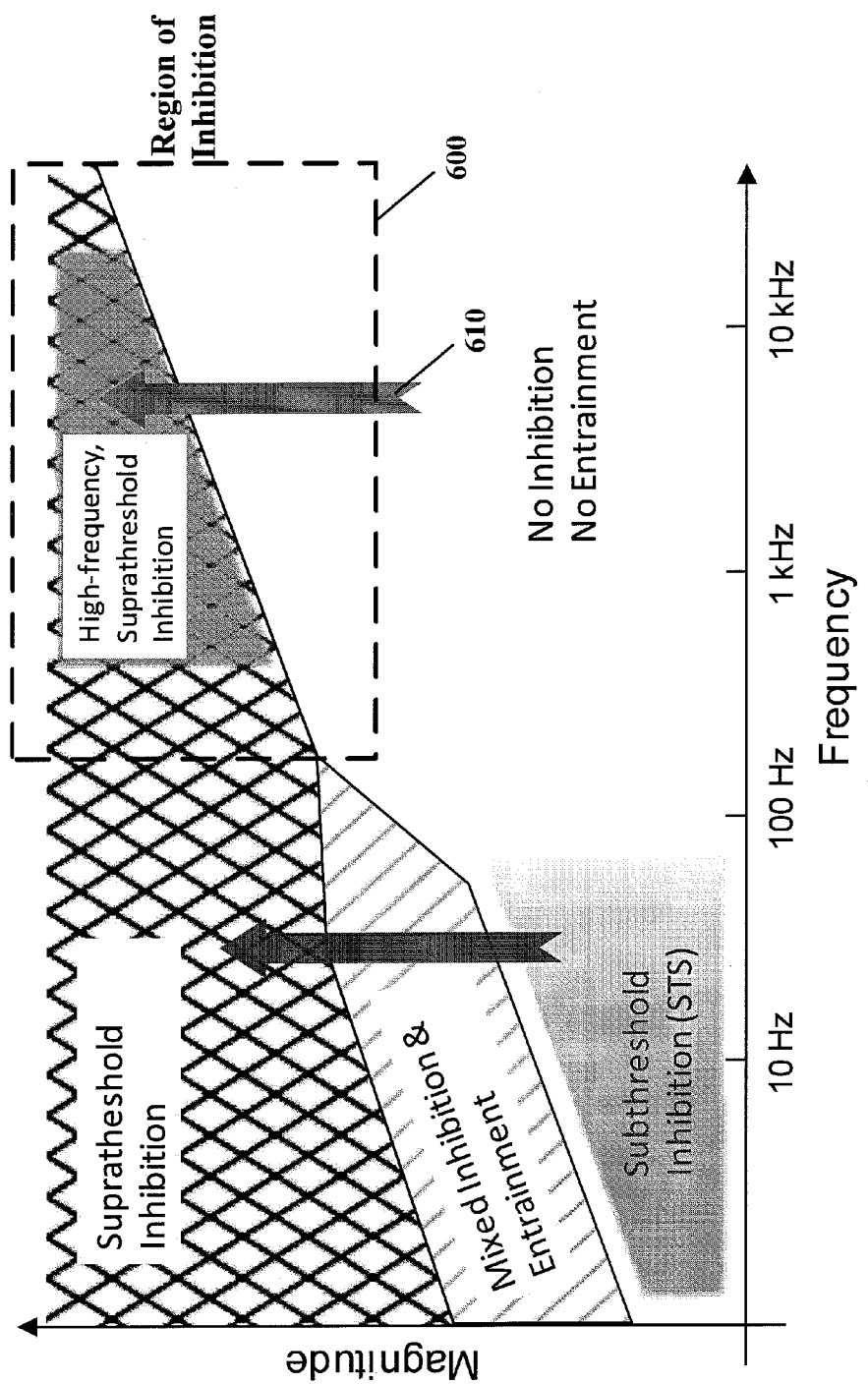
FIG. 6 shows an example comparison of various electrical inhibition modalities, consistent with various aspects of the present disclosure.

FIG. 6 shows a comparison of various electrical inhibition modalities. Subthreshold stimulation (STS) can be ineffective without precise timing of stimuli relative to action potentials in the tissue. Suprathreshold stimuli can be applied asynchronously (e.g., it can cause an initial action potential and subsequently maintain the tissue in a depolarized state). Utilizing higher frequencies, as shown in the region of inhibition 600, can be used to provide a well-defined response with varying amplitude 610. Surprisingly, subthreshold high frequency stimuli were not shown to cause entrainment. The amplitude and frequency thresholds highlighted in FIG. 6 can vary depending upon particular parameters, such as the tissue type.

Suprathreshold stimulation can be useful for avoiding the need to limit the injected current based upon a risk of entrainment. Thus, suprathreshold stimulation facilitates a broad range of applications by effectively operating within a wide margin of stimulation parameters. The particular threshold can vary with the system parameters and can even vary between the different tissue/cells at a target location. Thus, a given stimulation strength may be sufficient for some cells, but not for others. This can cause a depolarization/inhibition in some, but not all, of the target cells. Moreover, in in vivo situations, there can be a rapid decrease of current density resulting in only a small volume of tissue, close to the stimulation electrode, being depolarized/inhibited. Aspects of the present disclosure recognize that suprathreshold stimulation can be increased without causing entrainment. Thus, the upper limit to such stimulation can be dictated by safety factors (e.g., damage to tissue) or the power-providing capabilities of the device. Corresponding increases can therefore lead to large areas of effective depolarization/inhibition. This can be important to provide, for example, adequate blocking of conduction through the entire chamber wall.

Additional aspects of the present disclosure recognize that high frequency suprathreshold stimulation can be applied without synchronization with a particular action potential/beat/cardiac cycle. Such aspects allow for suprathreshold stimuli application at any time in a cardiac cycle. In particular, the application of the inhibition stimulus can generate a depolarization separate from the cardiac cycle and thereafter the tissue can be maintained in an inhibited state. If applied within the action potential, no extra depolarization is generated. In cases where this extra depolarization is not desirable, the application can be synchronized with the cardiac cycle.

Various aspects of the present disclosure are additionally directed toward quick onset and offset stimulation. Additionally, the stimulation is reversible, in certain embodiments of the present disclosure. Further, certain embodiments utilize stimulation to inhibit the tissue over long period of time. This finding is surprising based on STS, which typically inhibits for milliseconds to seconds, and the duration of inhibition with STS is not as well controlled (dependent on amplitude and onset timing, and varying across subjects).

Various aspects of the present disclosure are directed towards electrical stimulation protocols that trigger depolarization of cardiac and other electrogenic tissues. Such protocols can utilize high frequency bursts, which in some embodiments are biphasic, to modify the intracellular potential until threshold is reached and depolarization occurs.

Figure 7:
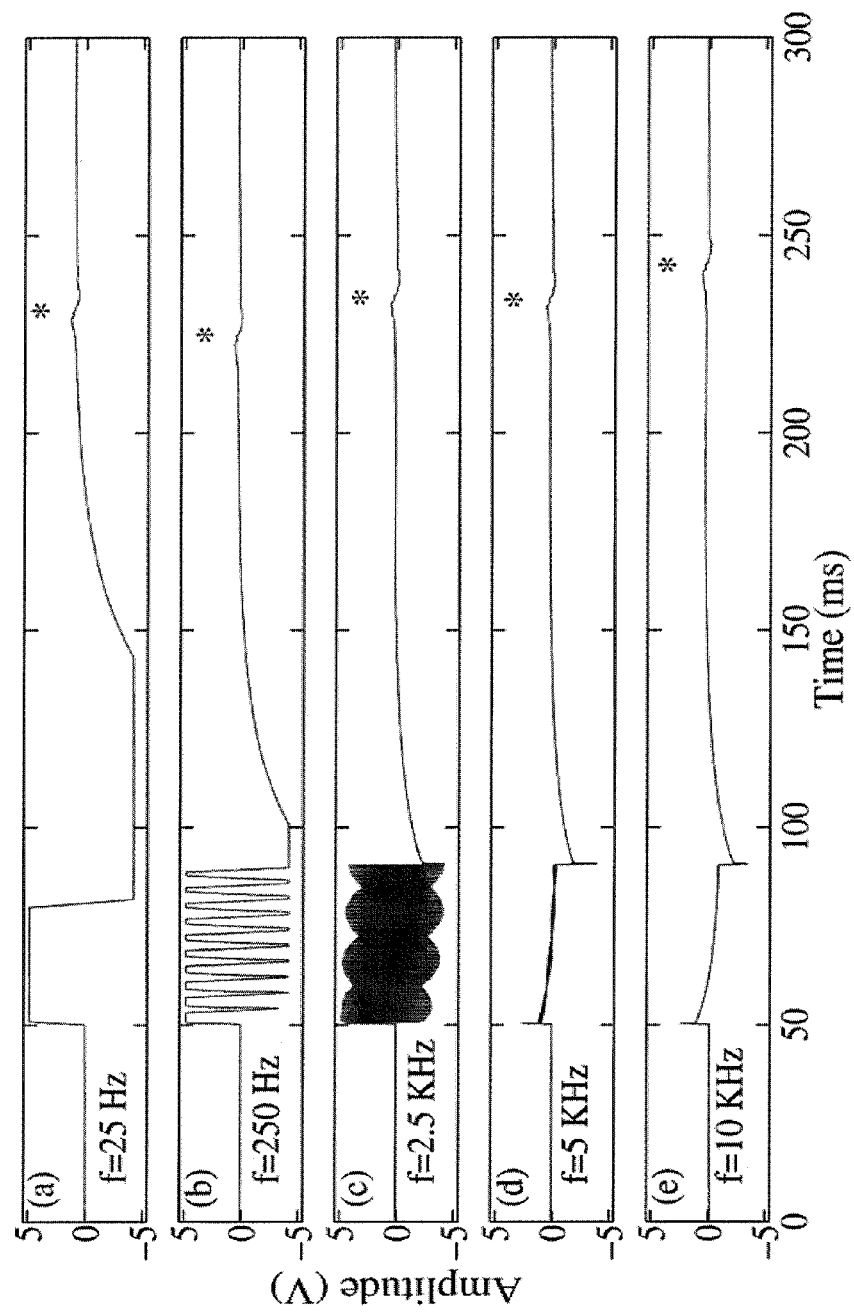
FIG. 7 is a graph that shows example results (in respective y-axis segments sharing a common time (or x) axis) of stimulation of HL-1 cardiac cells with a standard biphasic pulse (25 Hz) and bursts of increasing frequencies, consistent with various aspects of the present disclosure.

Effective stimulation with bursts of higher frequency biphasic (AC) square pulses is surprising considering that the cathodic phase (depolarization of the membrane) would typically be cancelled by the following anodic phase according to standard understanding of slow pulses stimulation mechanisms. FIG. 7 shows the stimulation of HL-1 cardiac cells using a biphasic pulse (25 Hz) and bursts of increasing frequencies. FIG. 7 shows aliasing in the 2.5 kHz trace, due to the limited sampling rate of the acquisition system (10 kHz). For 5 and 10 kHz, the limited bandwidth of the amplifier is filtering out the stimulus. In each case, the stimulus was able to stimulate the cells as seen by the action potential (*).

Figure 8:
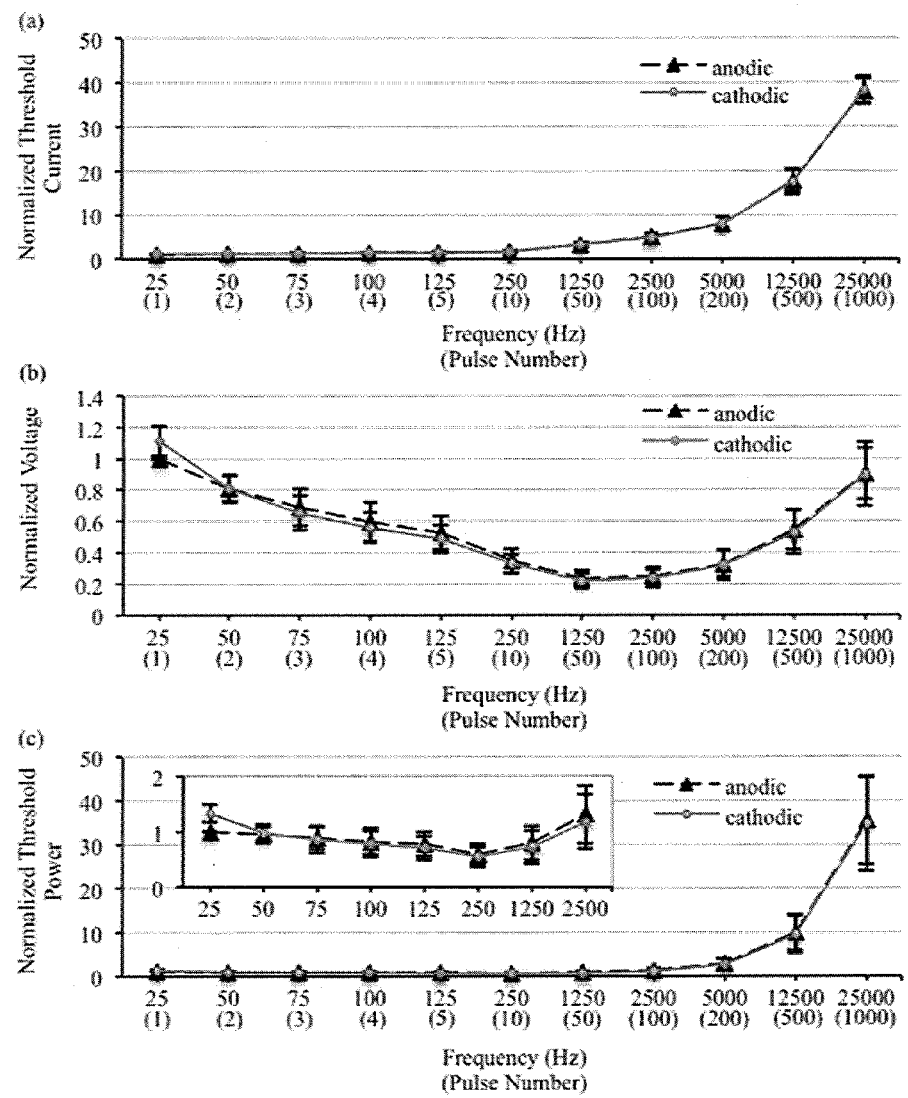
FIG. 8 (including respective graphs FIGS. 8(a), 8(b) and 8(c)) shows example stimulation thresholds for a pulse/burst of fixed duration, consistent with various aspects of the present disclosure, wherein each of FIGS. 8(a), 8(b) and 8(c) shows one such example.

FIGS. 8(a), 8(b) and 8(c) show respective stimulation thresholds for a pulse/burst relative to (a) current, (b) voltage, and (c) power. Current thresholds for high frequency depolarization are typically higher than simple biphasic pulses (pulse duration of 40 ms). Certain embodiments of the present disclosure take advantage of a decrease in effective electrode impedance relative to increases in stimulus frequency, thereby reducing the necessary voltage to provide a given current. Accordingly, high frequency stimulation at 2.5 kHz can require the same amount of power (current×voltage) relative to a corresponding biphasic pulse. Additionally, in certain embodiments, frequencies in the 100 Hz to 2.5 kHz range lead to lower power requirements, despite higher current thresholds. The lower voltages required to achieve stimulation in this range of frequencies (100-2.5 kHz), in certain embodiments, reduces the probability of irreversible electrochemical reactions at the electrode. Such embodiments provide increased safety of stimulation (especially for long-term stimulation), and reduced electrode wear.

Figure 9:
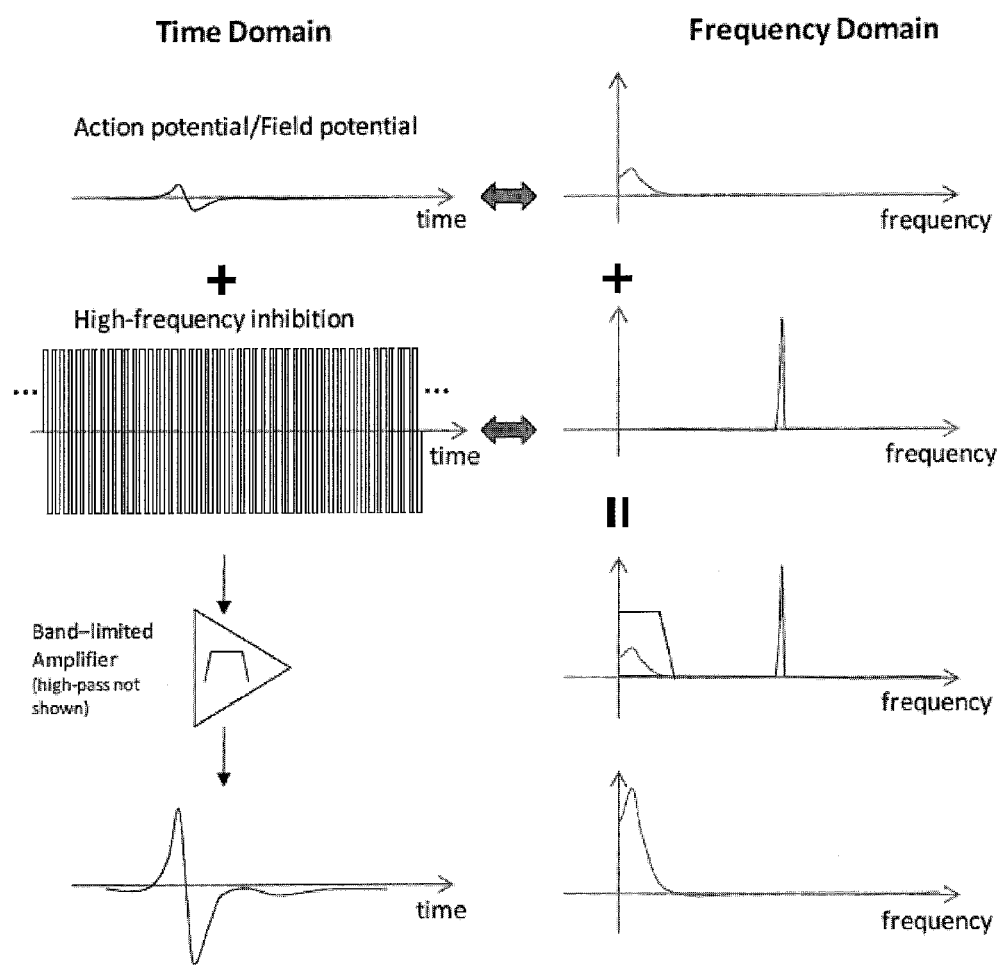
FIG. 9 shows an example depiction of the principle of decoupling of inhibition/blocking and recording using high frequency AC stimulation, consistent with various aspects of the present disclosure.

High frequency stimuli is effective in inhibiting depolarization, therefore, aspects of the present disclosure are directed towards a blocking stimulation that can be separated (non-overlapping) in the frequency domain from the action potential signals. For instance, cardiac action potentials can be detected at frequencies below 1-2 kHz, and the blocking/inhibiting stimulation can be effectively delivered at 5-10 kHz. Certain embodiments of the present disclosure therefore provide the ability to use one or more electrodes to simultaneously record/detect the cellular activity while applying conduction block. Aspects such as these are shown in FIG. 9 displaying decoupling of inhibition/blocking and recording using high frequency AC stimulation.

The various aspects of the present disclosure are not limited to cardiac tissue. For instance, the high frequency stimulation can be applied to other tissue types, such as neurons, pancreatic cells (beta cells), photoreceptors (application to retinal implant). The frequency ranges may be different depending on tissue types and applications. In certain embodiments, the high frequency stimuli are current-controlled, and in other embodiments, the high frequency stimuli are voltage-controlled. Further, the high frequency stimuli, as applied either via current or voltage, can be provided using any of various waveforms (e.g., square pulse, triangular, sine wave). Moreover, in various other embodiments, the high frequency stimuli are delivered through various type of electrodes (e.g., conductive, capacitive). Additionally, various embodiments of the present disclosure utilize an alternative to metal electrodes for the delivery of the AC currents via a dense photovoltaic cell array as substrate. This allows the localized delivery of the inhibition stimulus by focusing (or patterning) light on the surface. This approach alleviates the need for patterned electrodes on the surface, allowing more reconfigurable aspects of the system.

Various aspects of the present disclosure are directed towards use of high frequencies (e.g., >1 kHz) for inhibition that allow for the separation of the inhibition stimulus and cardiac signals in the frequency domain, by band-limited amplification and filtering.

In embodiments that utilize both electrical stimulation and recording (e.g., pacemakers, MEAs, neural implants), the recording of an action potential can be corrupted by the artifact of the stimulation. The stimulus, which can have a larger amplitude than the measured action (or field) potentials, can obscure the recording of these potentials during the application of the stimulus (amplifier saturation) and for a period of time after the end of the stimulus (electronic recovery from saturation, capacitive behavior of the electrodes and electrochemical recovery). This restricts the possibility to detect coinciding activity or to directly assess the outcome of stimulation. Aspects of the present disclosure achieve decoupling of recording and stimulation, resulting at a minimum in a dead time between the offset of the stimulation pulse and the start of the recording, typically of a few milliseconds to tens of milliseconds after the end of stimulus (depending on the stimulus amplitude and duration, electrode type, and tissue stimulated).

The artifact can be especially detrimental when the events to be recorded are simultaneous (or close in time) relative to the applied stimulus. Such embodiments facilitate the use of common circuitry for the stimulation and recording (e.g., blanking circuits). They can also reduce the need for complex charge balancing electronics or for complex signal processing (e.g., linear and non-linear filtering, template subtraction). Aspects of the present disclosure allow for separation of recording and stimulation, thus avoiding dead time during which recording cannot be performed (e.g., during the stimulus and typically for a few milliseconds to tens of milliseconds after the stimulus).

Various aspects of the present disclosure provide decoupling of stimulation and recording by applying a stimulus burst containing an oscillating wave at a frequency above the low-pass limit of a band-limited amplifier that is designed to filter the stimulus from the recording. Cardiac signals generally have frequencies that lie under 1 kHz. By stimulating cardiac signals at frequencies greater than 1 kHz (e.g., 5 kHz, 10 kHz, 25 kHz or 50 kHz), a frequency-based filtering/analysis can be used to separate the stimulus from an action potential. There is a number of possible filtering/analysis algorithms and circuits that can be used including, for instance, the use of Fourier transforms in the frequency domain.

In certain embodiments, envelope is shaped to provide further reduction of any remaining artifact. This can include the reduction of harmonics or frequency overlap associated with a lower frequency spread of the stimulation bursts. For instance, a triangular envelope corresponds to a squared sinc function in the frequency domain, compared to a simple sinc for a rectangular envelope, thereby reducing the power in side lobes that may still overlap with the band of amplified frequencies. Other embodiments of the present disclosure utilize engineered envelopes that optimize this reduction (e.g., Gaussian, triangular, hamming). In certain embodiments, based on the dependence of stimulation thresholds with frequency (higher frequencies have higher thresholds—see FIG. 8), and the dependence of the artifact on the separation between stimulation frequency and recording bandwidth, an optimum frequency can be selected in order to minimize the overall artifact. In other embodiments, without optimization, the artifact is reduced to comparable or lower amplitude than the AP of interest as shown in FIG. 9, thereby allowing the detection of this signal at any time.

Figure 10:
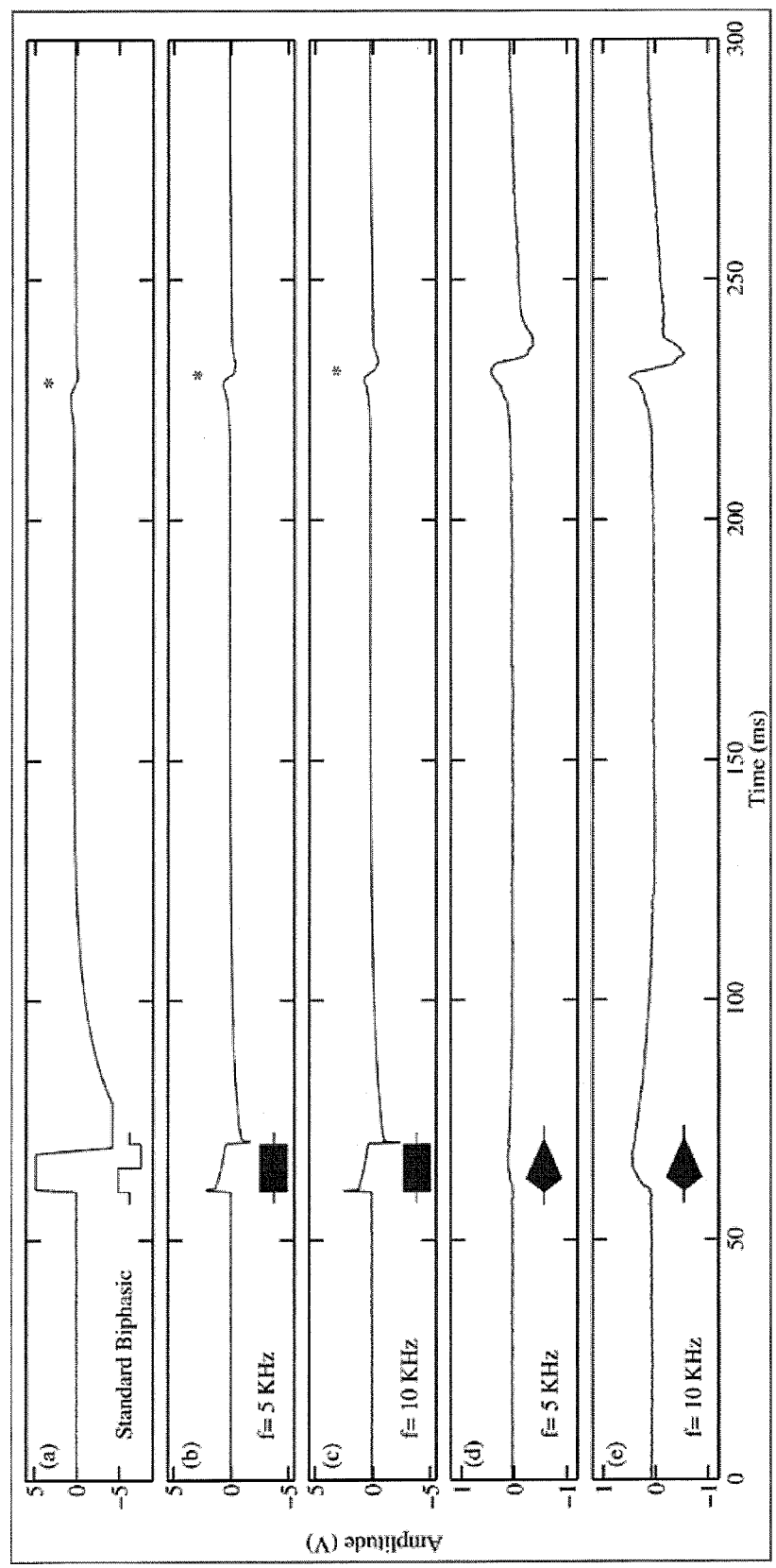
FIG. 10 shows an example of reduction of remaining artifact through burst envelope shaping, consistent with various aspects of the present disclosure.

FIG. 10 shows burst envelope shaping for reduction of remaining artifacts. Note the relative amplitude of the action potential (cardiac signal) with respect to the stimulus artifact. The larger stimulus at 10 kHz compared to 5 kHz reflects the higher amplitude required to capture the tissue at those frequencies.

Figure 11:
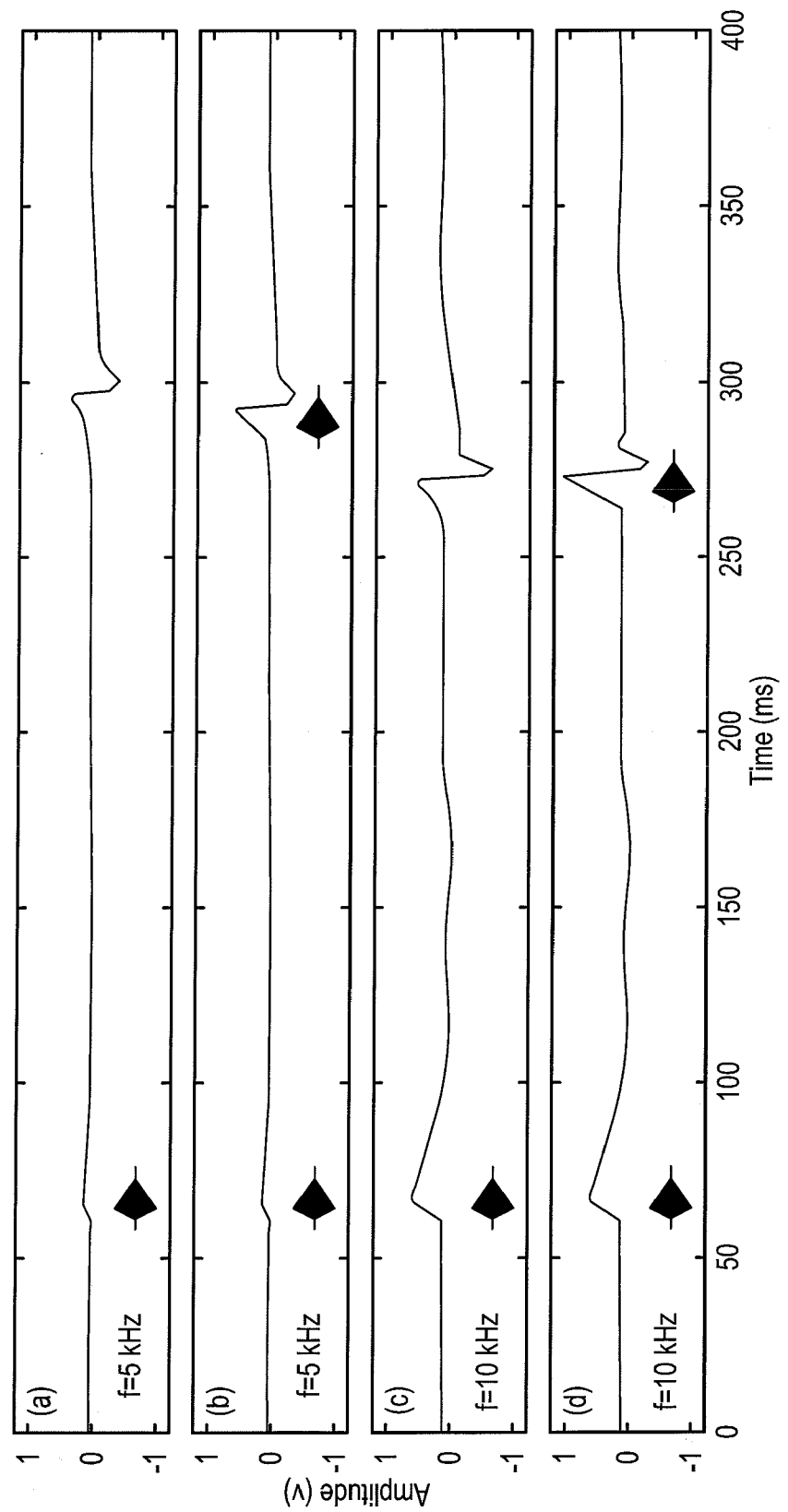
FIG. 11 shows example results of cardiac action potential during stimulation, demonstrating the ability to record during a stimulus, consistent with various aspects of the present disclosure.

The ability to reduce the stimulation artifact to comparable or lower amplitudes than the signal of interest also allows for, in various embodiments, the detection of the signal during the stimulation. FIG. 11 shows recording of cardiac action potential during stimulation with 10 ms bursts at 5 kHz in (a) and (b) and 10 kHz in (c) and (d). A first stimulus is given to elicit an action potential (a), (c). A second stimulus is timed to occur when the action potential reaches the recording electrode (b), (d), demonstrating the ability to record during a stimulus. While two different electrodes are used here for stimulation and recording, the same principle can be applied using a single electrode for both stimulation and recording. In certain embodiments, a software artifact reduction technique can be used, such as template subtraction or adaptive filter that will further reduce any remaining artifact if complete removal is sought.

In certain embodiments of the present disclosure, in achieving separation of signal and stimulus, the recording hardware (amplifier) is configured to enhance the linearity of the amplification throughout the amplification/filtering chain. This implies successive, lower gain, bandwidth-limited gain stages that prevent saturation of any of the amplifiers in the chain, especially at the front-end where the high frequency stimulus is not yet attenuated. Applying this type of arrangement avoids false observation of reduced artifact during stimulation, non-linear distortion of APs during and following the stimulus, and inability to detect the AP.

Figure 12:
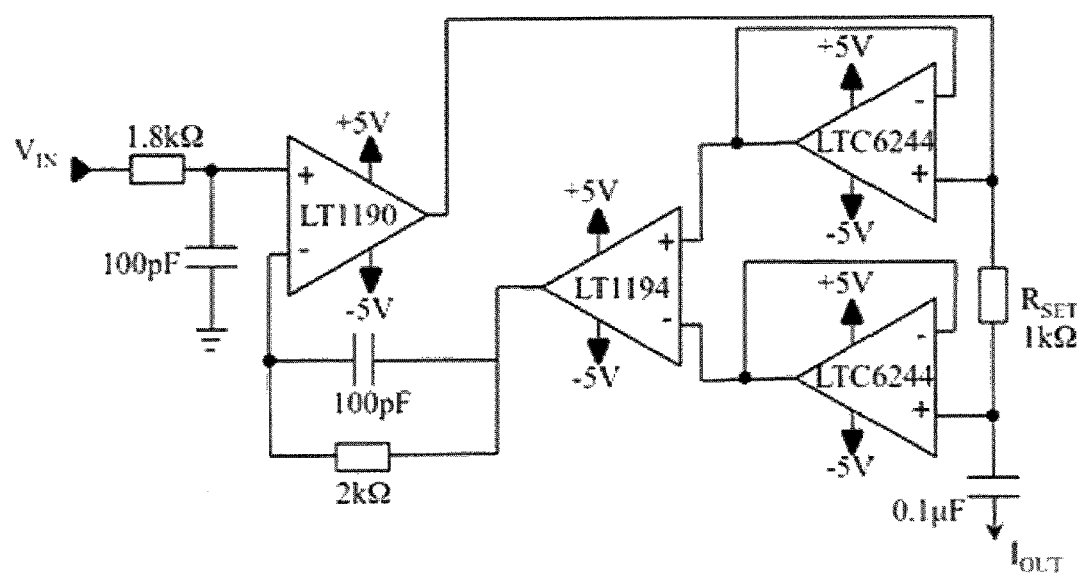
FIG. 12 shows another example schematic drawing of the voltage-controlled current source used for stimulation, consistent with various aspects of the present disclosure.

In certain embodiments, the recording hardware (amplifier) can be configured to improve the linearity of the amplification throughout the amplification/filtering chain. An example of such hardware is shown in FIG. 12, which depicts an example schematic drawing of the voltage-controlled current source used for stimulation, consistent with various aspects of the present disclosure. The linearity of the amplification can be achieved by limiting the amplification of the HF stimulus by the gain stages. The combination of lower threshold voltages at high frequency (as discussed above with reference to FIG. 8) and voltage division between the stimulation, recording and ground electrode, can be sufficient to limit saturation of the amplifier and resulting distortions. If saturation is not limited, signals recorded during stimulation could be strongly distorted or even completely attenuated. In certain embodiments, utilizing different amplifier architecture and filtering out the HF stimulus before amplification would allow even larger stimulus amplitudes to be tolerated without distortion. An embodiment utilizing such an arrangement can use the same electrode for stimulating and recording (in which case the full stimulus amplitude is applied to the amplifier front-end).

In certain embodiments, recording of cardiac activity can be performed via a separate electrode, and in other embodiments, recording of cardiac activity can be performed using the same electrode that delivers the stimulus. In embodiments using a recording electrode, the inhibition stimulus can be verified to determine if it has achieved its intent: to inhibit further depolarization and locally block the conduction of further action potentials. This verification increases considerably the reliability and confidence in the system, since it can be determined accurately if the tissue is inhibited. For instance, inhibition can be applied at a frequency exceeding 1 kHz (e.g., between 2.5 kHz and 500 kHz, 5 kHz and 200 kHz or 10 kHz and 100 kHz) while a frequency-based filter is configured to block the frequency of stimulation from a sensed signal. The filtered signal is then monitored to detect the presence (or absence) of action potentials.

Figure 13:
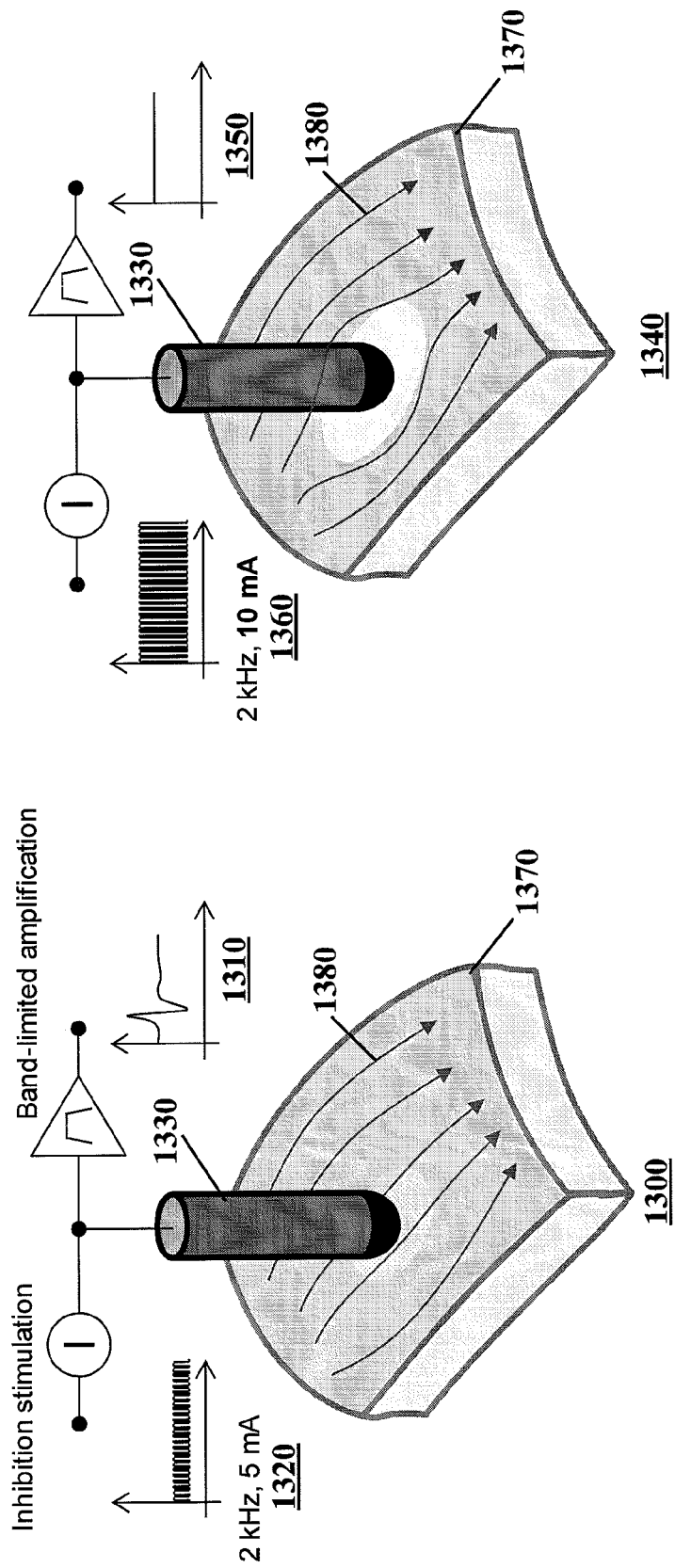
FIG. 13 shows an example illustration of simultaneous inhibition and cardiac activity recording, enabled by high frequency inhibition, consistent with various aspects of the present disclosure.

FIG. 13 illustrates an example of simultaneous inhibition and cardiac activity recording, facilitated by high frequency inhibition. The left portion 1300 of FIG. 13 shows an example of incomplete inhibition 1310 based on a low amplitude stimulus 1320 that is not able to completely depolarize/capture the volume under the probe 1330. As a result, an action potential occurs in the tissue, as measured by probe 1330. The right portion 1340 of FIG. 13 shows an example of complete inhibition 1350 based on a stimulus 1360 that is sufficiently strong so as to fully capture the tissue 1370. Since no action potentials are detected by the probe, the inhibition of the same is confirmed. In both portions of FIG. 13, the electrical prorogation 1380 is shown traveling through a tissue 1370. Embodiments of the present disclosure utilize recording electrodes that allows for the automatic adjustment of the amplitude of the stimulus in case of failed or incomplete inhibition.

In certain embodiments, the amplitude and frequency range of the stimulus are varied to a large extent and/or in response to feedback. Additionally, the shape or duty cycle of the waveform can also be varied. Further, as described above, the present disclosure is not limited to simulation of cardiac tissue, as other tissue types and organs can be stimulated.

Utilizing the ability to detect AP during the stimulation, various embodiments of the present disclosure are directed toward closed-loop control of the stimulus (e.g., duration, intensity, frequency and/or waveform). In certain embodiments, stimulation is applied at a particular location in the tissue to start depolarization. This tissue can be simultaneously measured to detect the effect of the stimulus. The closed loop systems can be designed to factor in other inputs as well. For instance, an electrocardiograph (ECG) can be used to determine the effectiveness of the delivered stimulus (e.g., to detect the presence of an arrhythmia or the effectiveness of pacing).

Figure 14:
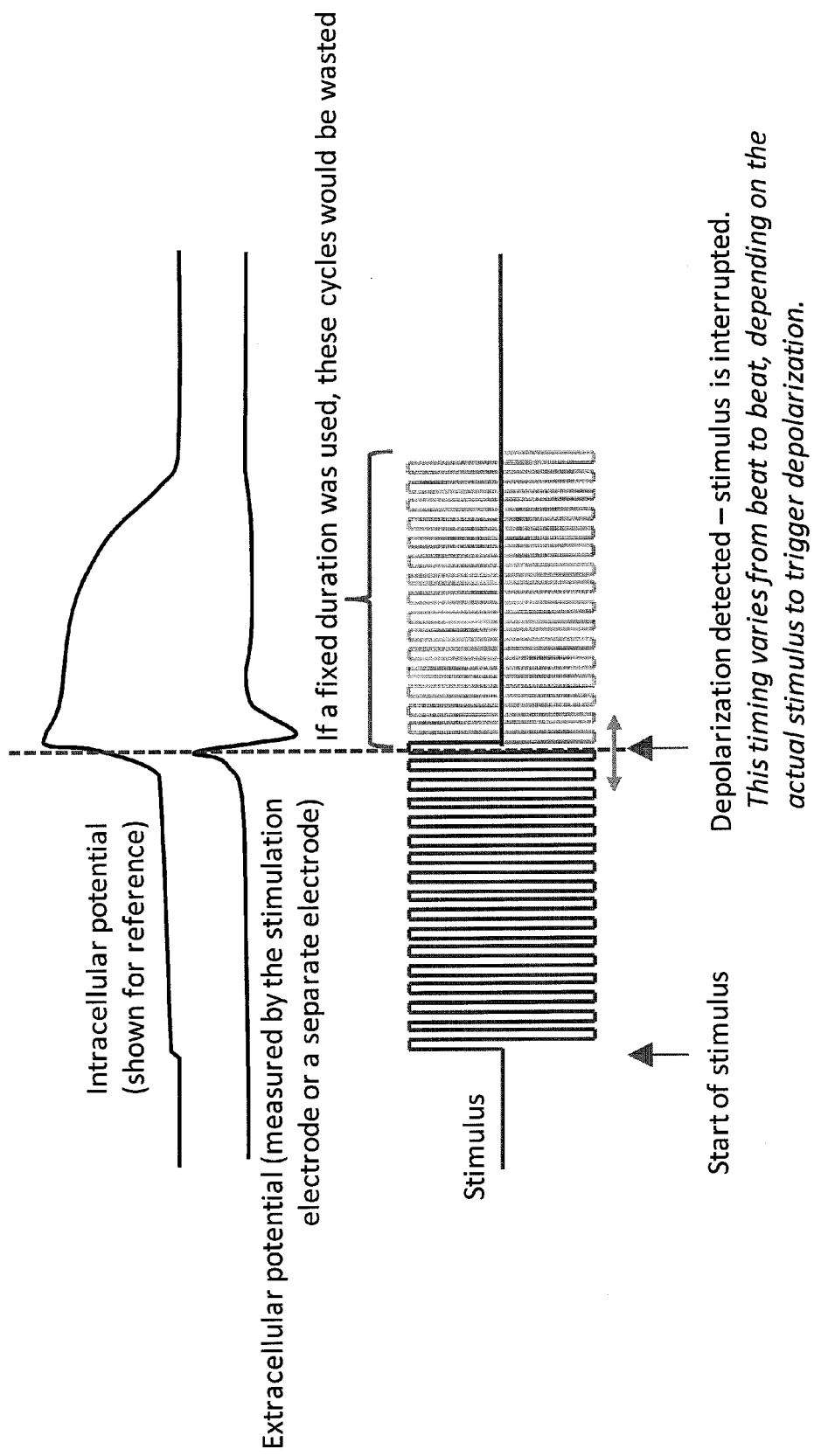
FIG. 14 shows an example of closed-loop stimulation based on the ability to detect precisely when the tissue depolarizes, consistent with various aspects of the present disclosure.

For instance, if the stimulus is intended to capture/pace the cardiac tissue, the stimulus can be stopped in response to the detection of an action potential. This can be useful for avoiding unnecessary stimulation and for reducing the amount of power drawn and delivered to the cardiac tissue. An example of this is illustrated in FIG. 14, which shows closed-loop stimulation where the stimulus is turned off in response to detecting precisely when the tissue depolarizes. In certain embodiments, such a concept can be utilized to deliver the exact amount of charge necessary to trigger each action potential. Without such a closed loop system, a system will generally be configured with a sufficient amount of leeway relative to the minimum amount of required stimulation. Without such leeway, the system runs the risk of not generating an action potential. The ability to actively control the delivery of stimulation facilitates the use of the electrical stimulus at levels at, or much closer, to such minimum amounts.

In certain embodiments, a pacemaker device implements a variation of closed-loop stimulation. This ensures reliable pacing by maintaining the stimulation up until the tissue is depolarized and then ceasing stimulation, thereby, decreasing the amount of stimulation (and power) used to pace/capture the cardiac tissue. These embodiments can also apply power-optimized pacing to synchronize the pacing by avoiding the application of stimulation to tissue that is already (or was recently) depolarized. These and other techniques can be used in combination and can be particularly useful for providing efficient (reduced power) pacing.

Certain embodiments of the present disclosure utilize the ability to detect action potentials during the stimulation to assess stimulation parameters compared to standard strength-duration curve establishment (lengthy process) or as a closed-loop control. Aspects of the present disclosure sense the exact threshold (duration needed at a fixed amplitude to trigger depolarization) on a beat-to-beat basis. By avoiding overstimulation, there is a lesser risk of bias/hysteresis. It is also much faster to configure the system, as a single beat can be used to assess the stimulation threshold. Such capabilities could be particularly beneficial when used in cell-based assays and associated drug screening. As a result, the efficacy of the stimuli can be assessed without necessarily performing a series of steps in which the duration and amplitude of standard pulses are swept over a defined range, and tissue response need not be recorded over an extended period of time for each such step.

A closed loop system can also be provided for inhibition of action potentials. In such a system, the stimulus can be controlled based upon feedback regarding the state of the stimulated cardiac tissue. For instance, the system can continually increase the stimulation level (or adjust other parameters) in response to detecting action potentials. Once the action potentials have ceased to be detected, however, the system can maintain the current stimulation level (or other parameters). This can also be reversed by starting the stimulation at a high level and gradually reducing until action potentials are detected.

As discussed above, aspects of the present disclosure are not necessarily limited to cardiac tissue, and can be applied to other tissue types (e.g., neurons, pancreatic cells (beta cells), photoreceptors (application to retinal implant)). Additionally, the frequency ranges may be different depending on tissue types and applications. While demonstrated in vitro, aspects of the present disclosure are applicable in vivo (e.g., as shown for pacemaker applications). High frequency stimuli may be current or voltage-controlled, of various waveforms (e.g., square pulse, triangular, sine wave), and delivered through various type of electrodes (e.g., conductive, capacitive).

Certain embodiments of the present disclosure are directed towards use of a microelectrode array for applying a high frequency stimuli. Further, in other embodiments, such a microelectrode array can be defined by a two-dimensional electrode shape on a surface. Such an arrangement includes application of high frequency stimulation, and therefore inhibition of cardiac cells, which provides spatiotemporal control of the conduction in two dimensions (e.g., cells) and two and a half dimensions (e.g., tissue slices). The electrically-controlled spatial blocking of conduction through local inhibition can be applied to any culture or tissue, and therefore can be used in tissues of animals or humans, which have differing geometries. Additionally, various aspects of the present disclosure allow for the blocking pattern to be turned on and off at-will, and additionally allow for altering of the blocking pattern on-the-fly by reconfiguring which electrodes deliver the inhibitory stimulus.

Figure 15:
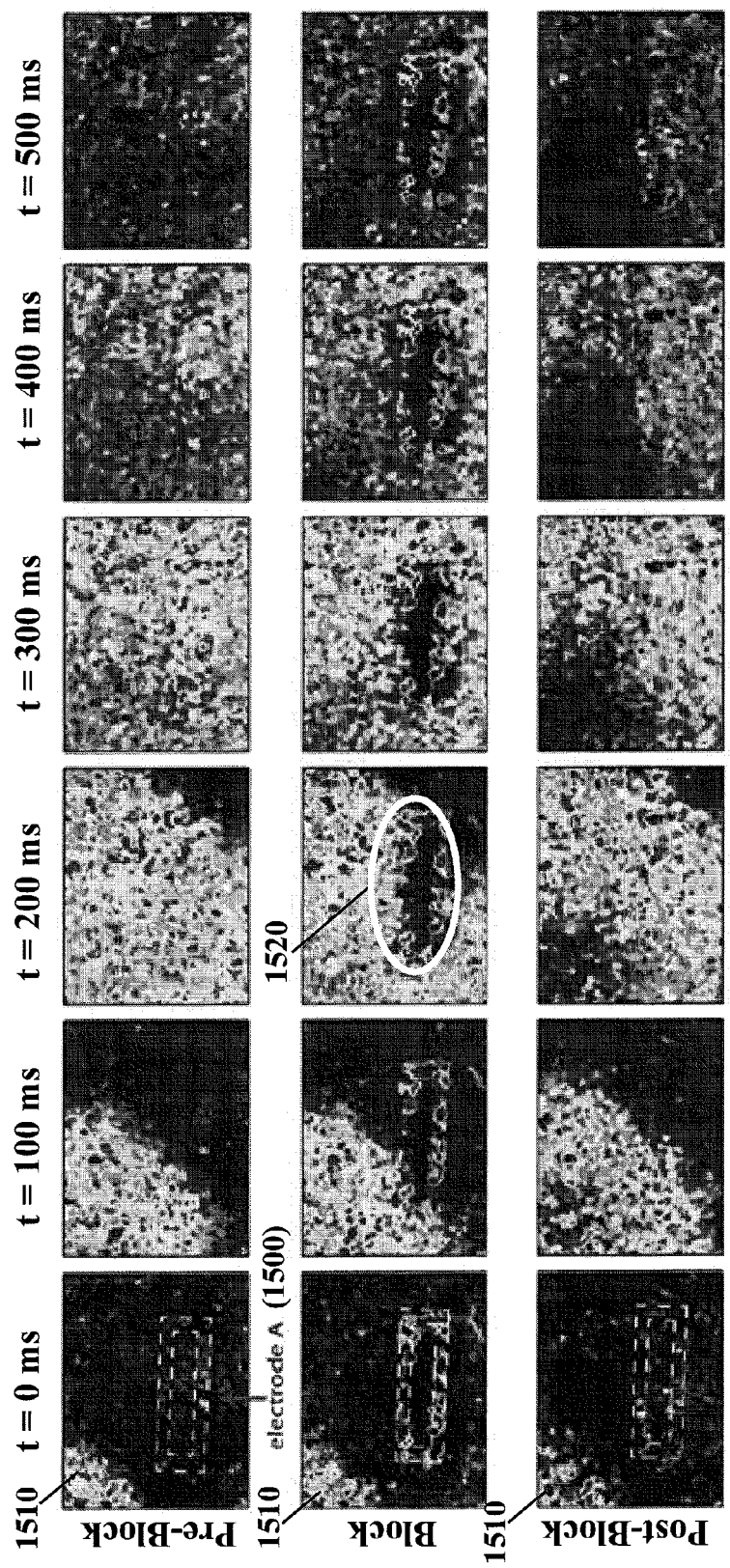
FIG. 15 shows an example time-lapse of Ca2+ fluorescence showing propagation of electrical activity before, during and after application of an inhibitory stimulus, consistent with various aspects of the present disclosure.

FIG. 15 illustrates the application of a conduction block in a culture of HL-1 cardiac cells. The blocking electrode 1500 isolates a patch of cells and prevents them from depolarizing during the block. The depolarization wave 1510 is forced to go around the block as indicated by the dark area within circle 1520. The depolarization wave 1510 is shown in a time-lapse of $Ca^{2+}$ fluorescence showing propagation of electrical activity before, during and after application of the inhibitory stimulus. Complete reversal is achieved within a beat upon termination of the stimulus. Complex conduction patterns (planar wave fronts, wave front with precisely-defined curvature, junctions) can be readily and reproducibly induced in cultures or sample tissues for specific research and drug assays.

An arrhythmia alters the flow of the electrical propagation of the stimulus. Some types of arrhythmia are related to re-entry pathways—abnormal conduction path leading to self-sustained loops of depolarization. This type of re-entry pathway is shown in FIG. 16 in an illustration of cardiac tissue 1600 with a normal electrical propagation 1610 (left), and abnormal electrical propagation 1620 (right). Aspects of the present disclosure relate to the use of high frequency stimulus to terminate such re-entry pathways. In particular, a stimulation electrode can be located near the abnormal electrical propagation 1620 and used to block the re-entry pathway by inhibiting conduction. This can have an effect that is similar to ablating the same tissue, but is reversible and also non-destructive.

Thus, the ability of inhibiting excitability (and therefore blocking conduction of action potentials in cardiac tissue), as discussed above, can be used to block such re-entry pathways for example, in real-time, localized alteration of conduction, from termination of re-entry, and defibrillation. This can be done in response to detection of the dysfunction, which can be particularly useful for treating sporadic dysfunction on an as-needed basis. A similar mechanism can be used to treat fibrillation, e.g., by inhibiting action potentials in the entire ventricle.

Catheter ablation is a successful technique to treat conduction abnormalities leading to tachycardia, flutter or fibrillation. It consists of locally (but permanently) altering (usually blocking) conduction by scarring tissue through thermal treatment. The thermal treatment is delivered by radiofrequency (RF, heating the tissue), or cryogenically (cold probe, freezing the tissue). Some procedures involving delicate pathways make the use of RF ablation too risky. For instance, ablation in the AV node region (for treatment of AV nodal reentrant tachycardia—AVNRT), if not guided properly, could result in a permanent AV block, requiring the implantation of a pacemaker. Cryo-ablation is typically used in these cases, as temporary blocks can be achieved by lowering the temperature enough to block conduction, but not enough to damage irremediably the tissue. This cryo-mapping provides a very useful guiding mechanism for ablation. RF ablation does not have a similar guidance mechanism.

Figure 17:
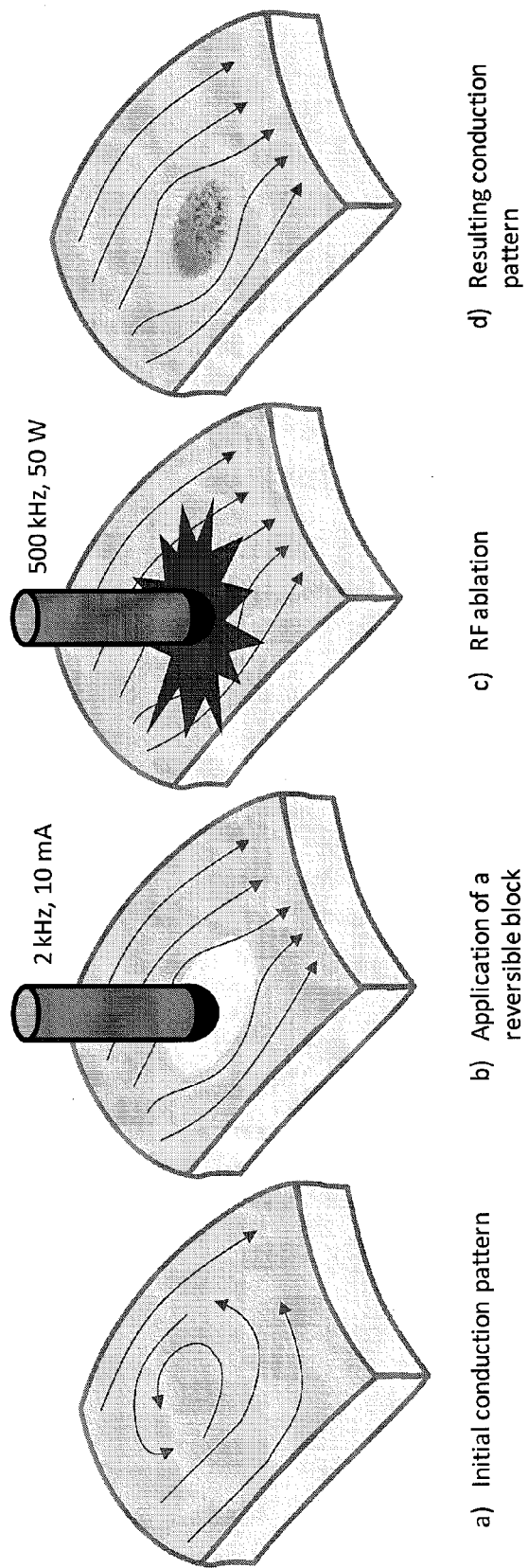
FIG. 17 shows guidance of RF ablation by temporary conduction blocks, consistent with various aspects of the present disclosure.
Figure 18:
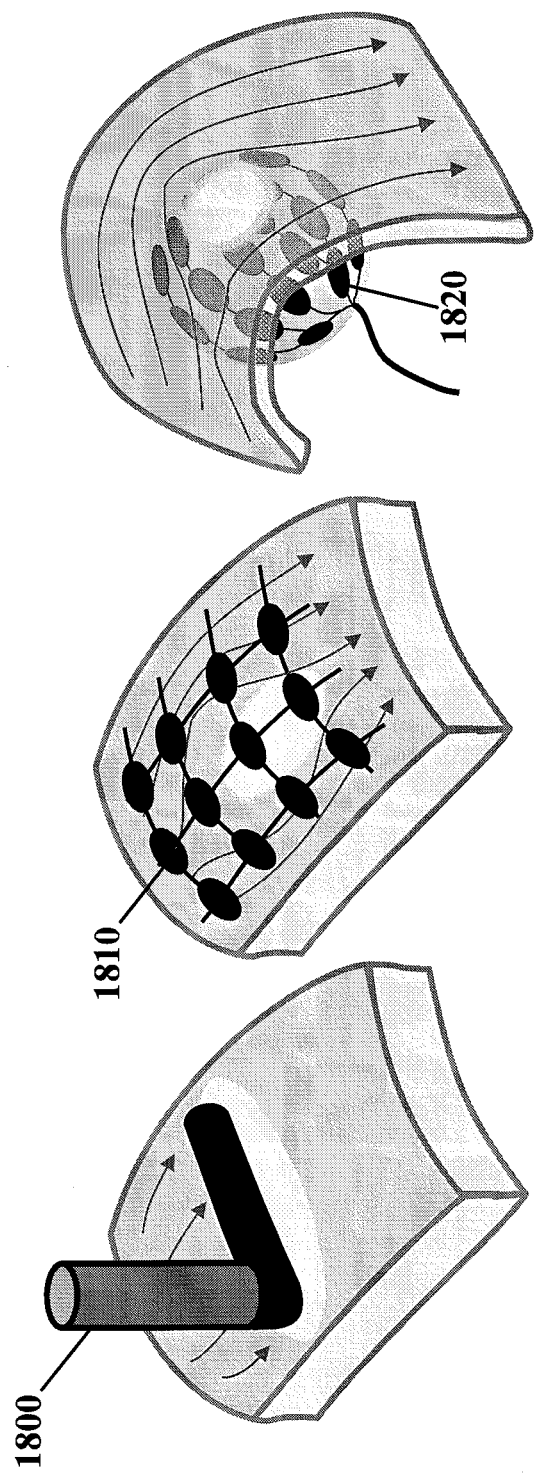
FIG. 18 shows example blocking patterns using different electrode geometries, consistent with various aspects of the present disclosure.

In certain embodiments of the present disclosure, high frequency (1-10 kHz, typically) suprathreshold cardiac mapping is used with a catheter with an adaptation (e.g., by firmware) of the stimulation waveform. An example of a guided RF ablation procedure is illustrated in FIG. 17, which depicts detection of an initial conduction pattern. Subsequently, an application of a reversible block, consistent with various aspects of the present disclosure, is applied. RF ablation then occurs, and a normal resulting conduction pattern results. Certain embodiments of the present disclosure utilize a complex pattern of blocks applied by designing specific electrodes/catheters. FIG. 18 shows possible example electrode configurations for such an application. For instance, in certain embodiments, as illustrated in FIG. 18, a long electrode 1800 is used to stimulate a line block. In certain embodiments, an array of electrodes can be used. For instance, FIG. 18 shows use of an epicardium mesh electrode 1810. FIG. 18 also shows use of an endocardium balloon electrode 1820. Both the epicardium and endocardium can be used to stimulate random patterns.

In certain embodiments, suprathreshold stimulation is applied utilizing an implantable device for local and transient disruption of abnormal conduction through inhibition of excitation. Embodiments utilizing an implantable device provide a large operational margin (frequency, amplitude). Further, an implantable device (e.g., a pacemaker) with traditional leads, in certain embodiments, is used with inhibition to locally affect conduction at the lead contacts. In certain embodiments, an implantable device is connected to more elaborate electrodes (e.g., mesh or socks) that provide complex patterns of conduction block in order to disrupt an episode of fibrillation or tachycardia. In the case of fibrillation, such an arrangement eliminates the need to utilize a high voltage shock.

Moreover, various aspects of the present disclosure are directed towards methods for modeling cardiac re-entry arrhythmia. These methods utilize a propagating depolarization wave in cardiac tissue by providing an electrical stimulus at a first location in the cardiac tissue. Additionally, the propagation of the depolarization wave is directed back to the first location by inhibiting depolarization of cardiac tissue using high frequency electrical stimulus applied to portions of the cardiac tissue and thereby creating a re-entry arrhythmia. In certain more specific embodiments, methods for modeling cardiac re-entry arrhythmia include steps of providing a candidate drug to the cardiac tissue and monitoring the depolarization wave and re-entry arrhythmia. Further, in certain embodiments of the methods for modeling cardiac re-entry arrhythmia, the high frequency electrical stimulus is provided at a frequency exceeding 1 kHz and less than 50 kHz.

Figure 19:
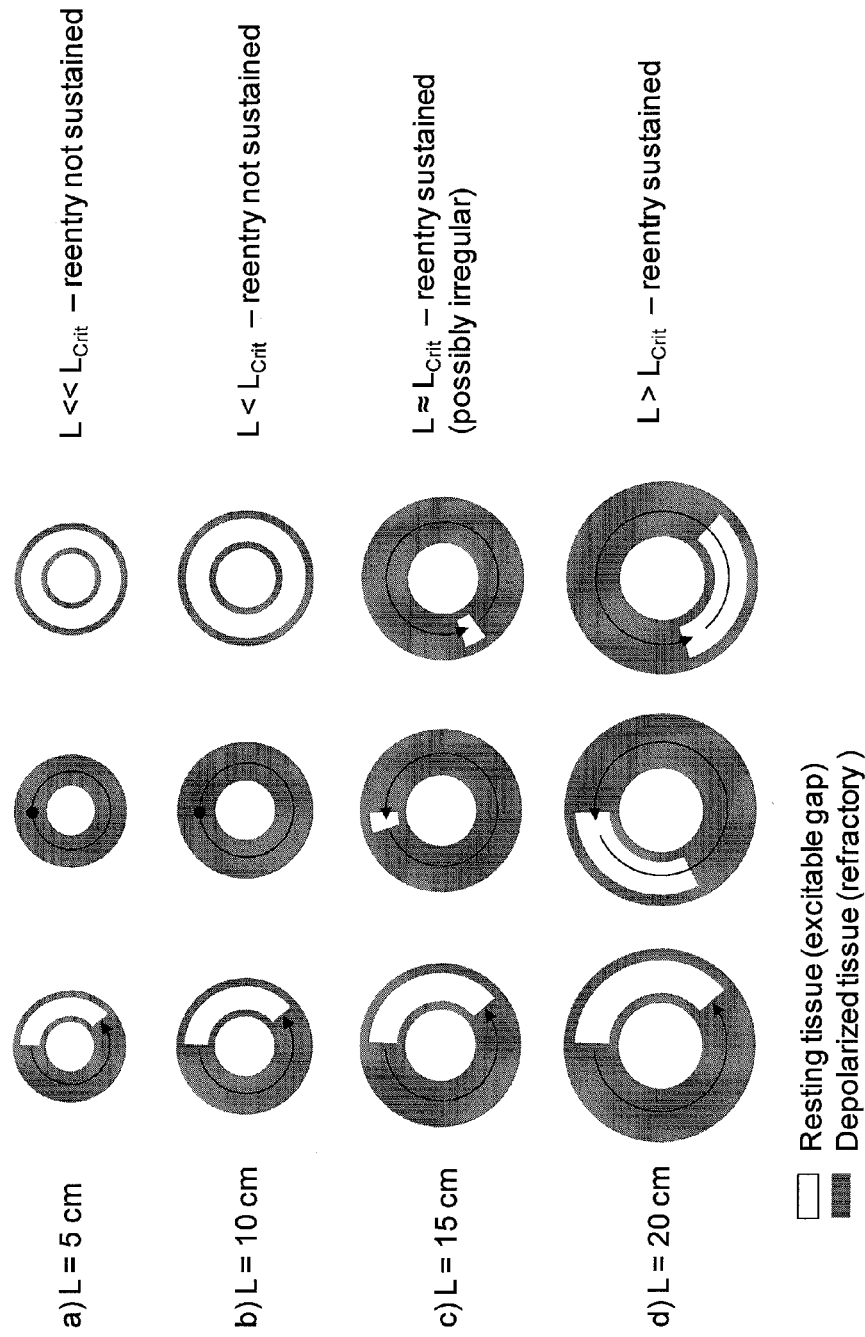
FIG. 19 shows an example illustration of un-sustained (a, b) and sustained (c, d) re-entry in rings of increasing diameter, consistent with various aspects of the present disclosure.

These re-entries can be found in tachyarrhythmias and some types of atrial fibrillation. Susceptibility to such arrhythmia is an important factor in risk assessment and stratification. Evaluation of this susceptibility involves the assessment of several conduction and action potential-related parameters: the conduction velocity (CV, in cm/s), the effective refractory period (ERP, in ms), the cycle length (CL, in ms) and the wavelength (WL, in cm). All four parameters are related and define the susceptibility of conduction paths to sustain re-entry. If the path is too short (L<WL), the tissue is still refractory when the wave front arrives, terminating the propagation. At the correct length (L≈WL), the tissue is now able to depolarize again, sustaining the re-entry. This critical length is related to the cycle length through the conduction velocity, and also depends on the effective refractory period of the tissue. This is illustrated in FIG. 19 which shows unsustained (a,b) and sustained (c,d) re-entry in rings of increasing diameter. The smallest ring sustaining re-entry corresponds to the minimum cycle length supporting re-entry. Smaller rings do not support re-entry. Measurement of occurrence and characteristics (period, conduction velocity) of re-entry in rings of various diameters provides key information on the susceptibility of the tissue to re-entry, and can offer, in certain embodiments of the present disclosure, an assay for drug screening.

Figure 20:
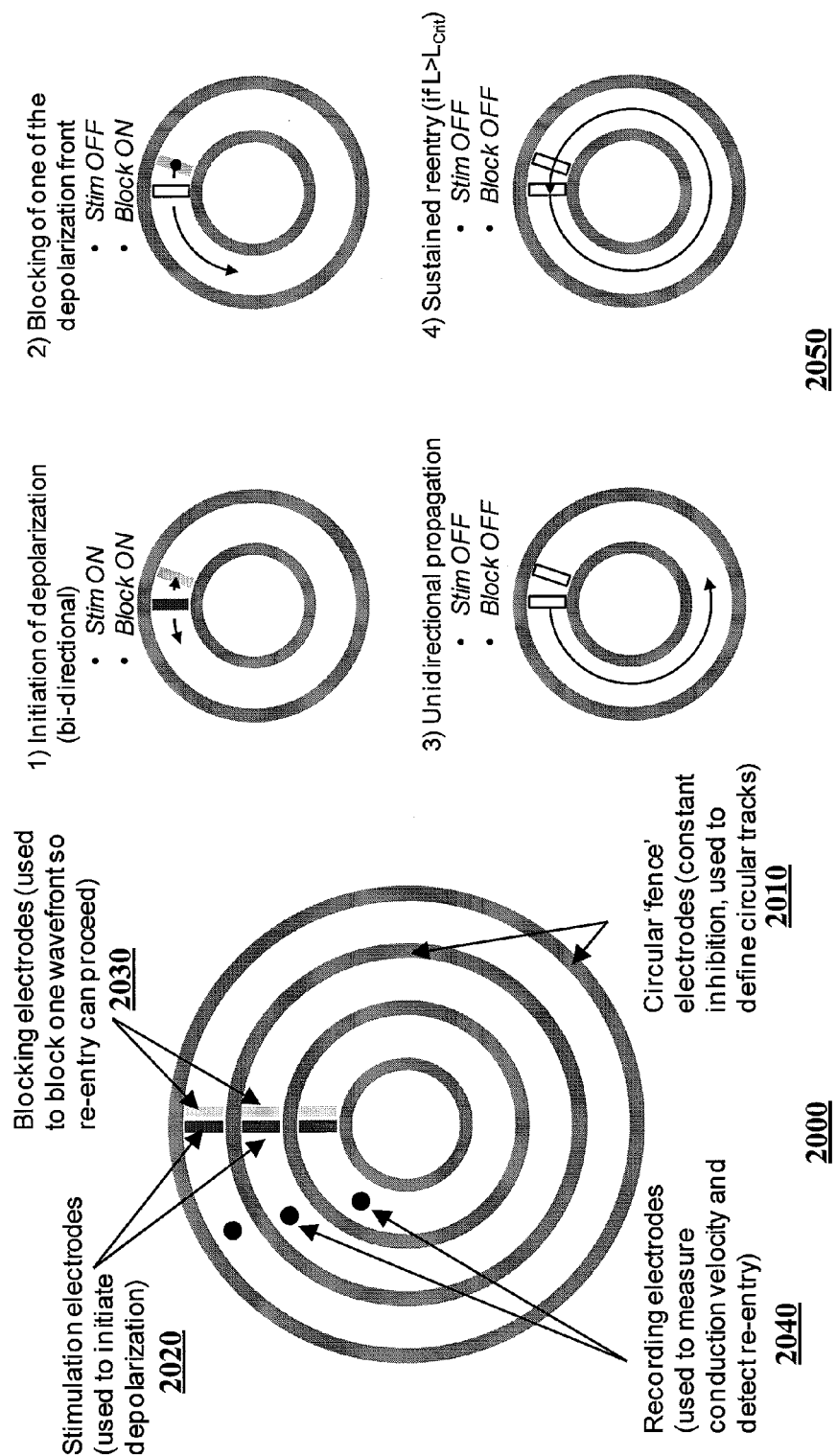
FIG. 20 shows an example of realization of a re-entry assay structure, consistent with various aspects of the present disclosure.

Aspects of the pressure disclosure relate to the use of electrically-defined rings of various diameters in a cell culture or tissue slice in order to quantitatively assess these parameters in a rapid, reproducible assay. The inhibition of excitability provides the definition of virtual rings in plain, non-patterned cultures or tissues. FIG. 20 shows an example of realization of a re-entry assay structure, consistent with various aspects of the present disclosure. Rings of various diameter/length can be readily defined in arrays of rings of increasing diameters, or, in certain embodiments, with concentric rings as shown in the left portion 2000 of FIG. 20. FIG. 20 shows one possible embodiment that shows use of blocking electrodes 2010 for ring creation, stimulation electrodes 2020 to initiate bi-directional wave fronts in each ring, blocking electrodes 2030 to stop one of the fronts, and recording electrodes 2040 to detect the wave front, measure the conduction velocity, and detect re-entry. An example timing of the electrodes is illustrated in the right portion 2050 of FIG. 20, which illustrates the timing of stimulation and blocking electrodes to reproducibly initiate a unidirectional wave front in each ring, consistent with various aspects of the present disclosure In certain embodiments, various aspects of the present disclosure utilize an assay to find the smallest ring sustaining re-entry, providing the wavelength, measure re-entry period, giving the cycle length and effective refractory period, and measure the time delay between two recording electrodes (or a stimulation and a recording) in the same ring, which gives the conduction velocity, knowing the ring diameter. As a diagnostic, these four parameters largely define the susceptibility of the tissue to re-entry. Therefore, various aspects of the present disclosure can test for the occurrence of and susceptibility to re-entry under various drug conditions in a repeatable fashion. Stable as well as irregular patterns can be measured and assessed. In certain embodiments, an assay, consistent with various aspects of the present disclosure, are mass produced on low-cost printed circuit board. Also, note how the separation in frequency of the blocking and excitation stimuli and cardiac signal makes such fully-electrical approach possible.

A number of experimental devices and tests are described herein. These experiments support a wide variety of additional embodiments and variations thereof and are not limiting. Consistent with one such experiment, extracellular stimulation of cardiac cells was utilized in vitro using bursts of high frequency alternating square wave, the ability of high frequency stimulation is demonstrated by reliably capturing and pacing HL-1 cardiomyocytes cultured on planar microelectrode arrays (MEA). The experimental investigation demonstrated the influence of stimulation frequency, burst duration and phase sequence on stimulation thresholds. Using high frequency stimulations, significant artifact reductions through frequency-domain separation were found. Further, the ionic mechanisms behind these stimulations use a single cell computer model.

In certain embodiments, lower potentials required for stimulation benefit long term applications by reducing electrode voltage and the probability of irreversible electrochemical reactions. Additionally, the reduction of stimulation artifacts to amplitudes lower than the recorded action potentials, achieved by simple frequency-domain separation, allows the detection of cardiac signals even during stimulation.

Figure 21:
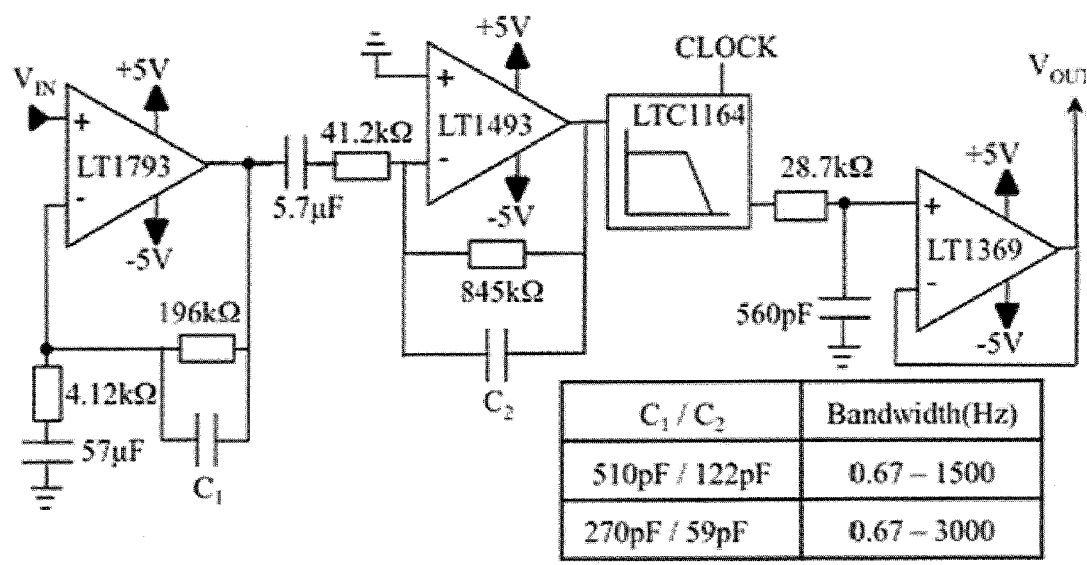
FIG. 21 shows an example schematic drawing of the recording circuitry with two different bandwidth options with successive, bandwidth limited amplification stages that limit saturation of the amplifiers, consistent with various aspects of the present disclosure.

The MEAs utilized in these experimental embodiments included a 6×6 array of platinum electrodes on a glass substrate. Microelectrodes were 22 μm in diameter and spaced by 100 μm. Additional larger electrodes were located on each side of the recording array for electrical stimulation. Signals were conditioned using a modified 36-channel custom recording system, as shown in FIG. 21. The signal path consisted of a two-stage, band-limited (1.5 or 3 kHz) amplifier with a gain of 60 dB, 0.7 Hz $1^{st}$ order high-pass filter, and an eighth-order low-pass filter at either 1.5 or 3 kHz. Thirty-two channels (four corner electrode excluded) were then digitized with a 12-bit resolution at 10 ksps (DAQ16/330, Measurement Computing, Norton, Mass.), and processed by a custom-designed visualization and extraction tool, written in Matlab™ (The MathWorks; Natick, Mass.). The eight-order low-pass filter ensured that no aliasing of the high frequency stimulus took place in the experiments aimed at quantifying the artifact reduction. In each case (5 kHz stimulus with 1.5 kHz cut-off, 10 kHz stimulus with 3 kHz stimulus), more than 80 dB of attenuation was provided, enough to satisfy the requirement for a 12-bit resolution (equivalent to 74 dB of dynamic range). This was independently verified during the experiments with an oscilloscope.

Stimulation signals were generated using a signal generator, and supplied to a custom-made voltage-controlled current source (similar to the arrangement shown in FIG. 12), to provide current stimulation (the current amplitude is set by $R_{SET}$ and equal to $I_{OUT}=V_{IN}/(10 \times R_{SET})$ with decoupling capacitors not shown). The voltage-controlled current source was based on a design from Linear Technology AN-47, adapted to provide sub-μA resolution. The current source used a high-speed operational amplifier sourcing or sinking current through a sense resistor in series with the grounded load. The current, sensed by a differential amplifier with inputs buffered by two low-input bias current op-amps, is fed back to the LT1190 to provide precise, closed-loop control of the current. The configuration resulted in a slew rate of 100 μA/μs. For burst envelope shaping, envelope waveforms were generated by data acquisition card, and multiplied with a square AC signal at the defined frequency with an AD734 multiplier circuit. The output of the multiplier was then fed to voltage-controlled current source to generate corresponding stimulation current. During all the experiments, the voltage on the stimulation electrode was monitored on an oscilloscope to verify appropriate waveforms and amplitudes, and peak amplitude was recorded.

The experiments were performed at room temperature. Electrical stimuli were applied through one of the large stimulation electrodes using current-controlled stimulation. High frequency stimulation was performed with bursts of biphasic square waves, where the pulse frequency ranged between 25 Hz and 25 kHz. In a 40 ms burst, these frequencies corresponded to increasing pulse numbers from 1 to 1000. Pacing thresholds for strength/duration curves were measured for burst durations of 5, 10, 20, 40 and 80 ms, where bursts of increasing pulse counts were used to facilitate comparison with single biphasic pulses. Pacing rate was set to overdrive the spontaneous beating (if any), and varied between 1 and 2 Hz at 100% capture fraction. Pacing stimuli were delivered starting at 5 μLA peak-to-peak (corresponding current density 25 μA/mm$^2$) and increased in 1-10 μA steps until 100% pacing capture was attained. Stimulations lasted 60 seconds to ensure stability of thresholds. Each cell culture was exposed to bursts starting with both anodic and cathodic phase. Stimulation with single biphasic pulse (both anodic-first and cathodic-first phase) was also performed to provide a comparison between standard single pulse stimulation and high frequency stimulation.

Artifact reduction experiments were carried out with two different sets of recording bandwidths and stimulation frequencies. Extracellular cardiac signals generally have components between 1 Hz and 3 kHz, but primary frequencies lie under 1 kHz. Hence, the first bandwidth was chosen between 0.67 Hz and 1.5 kHz (referred to as BW1) to record the primary frequencies, and the second one was chosen between 0.67 Hz to 3 kHz (referred to as BW2) to record a broader cardiac signal spectrum. Stimulation frequencies were then chosen higher than their corresponding recording bandwidths, namely 5 kHz for BW1 and 10 kHz for BW2. These frequencies provide enough separation between the recording bandwidth and stimulation frequency to allow for filtering out the stimulation by band-limited amplification and low-pass filtering. Burst envelope shaping using a triangular waveform was used to further reduce the artifacts. Stimulus duration was set at 10 ms for all artifact reduction experiments.

For the demonstration of simultaneous stimulation and recording, the following stimulation protocol was implemented: a first stimulus was given to trigger an action potential, and the relative timing of the action potential detected on the recording electrodes with respect to the applied stimulus was noted. Based on this propagation time, a second stimulus (with the same amplitude) was applied at the same time that the action potential triggered by the first stimulus reached the recording electrodes. The second stimulus did not generate any action potentials due to refractoriness, but allowed us to test whether the action potentials could be recorded during a simultaneous stimulus.

To investigate the possible mechanisms behind high frequency stimulation and the role of specific ion channels, simulations were performed using the mathematical model of a single human atrial myocyte described by A. Nygren, C. Fiset, L. Firek, J. W. Clark, D. S. Lindblad, R. B. Clark, and W. R. Giles, "Mathematical model of an adult human atrial cell: The role of K+ currents in repolarization," *Circ. Res.*, vol. 82, pp. 63-81, 1998, which is fully incorporated herein by reference. This model was based on averaged voltage-clamp data recorded from isolated single myocytes. It is based on a Hodgkin-Huxley-type model for the sarcolemma, and a fluid compartment model including intracellular, cleft and extracellular spaces. The model also accounted for changes in ionic concentrations in the cytoplasm and sarcoplasmic reticulum.

Transmembrane stimulation was simulated at the same frequencies as the experiments using 40 ms burst duration with both anodic-first and cathodic-first phase. Stimulus was applied between t=10 ms and t=50 ms, and typical simulation duration was chosen as 0.5 s to allow repolarization of the cell after the stimulus. The reported simulations used a time step of 1 µs, although convergence of the results was validated using smaller time steps. At each frequency, corresponding thresholds were found, and the role of individual ionic currents was determined.

All statistical data are shown as mean±standard deviation. Error bars in the figures represent the standard deviations. The n values in the text and figure legends indicate the number of independent experiments, i.e., number of separate MEAs or HL-1 cultures.

As described previously, the ability of biphasic square-wave bursts to trigger action potentials was demonstrated. Stimulations of HL-1 cardiomyocytes were performed with standard single biphasic pulse (corresponding to 25 Hz) and bursts of increasing frequencies for a fixed duration of 40 ms (corresponding to an increasing pulse number from 2 to 1000). Bursts starting with both cathodic (n=7) and anodic (n=8) phase were used. In each case, the stimulus was able to excite cells as seen by the recorded action potentials. Current thresholds for high frequency stimulations increased with higher frequencies and were typically higher than the threshold for single biphasic pulses ($I_{p-p}$=8.8±2.6 µA). The thresholds were similar for bursts with initial cathodic and anodic phase. Overall, high frequency stimulation was demonstrated in more than 30 experiments (cultures).

Without being limited by theory, the simulations and experiments suggest that a similar result could be achieved by delivering the stimulus electromagnetically (e.g., without the need for a direct current path between the stimulating electrode and the stimulated tissue). Adjustments to the delivered stimulation profile can be implemented for the electromagnetic stimulus in order to reach a suitable result. For instance, the electromagnetic stimulus can be incrementally increased (or decreased) to determine a threshold stimulus level for the tissue and particular application.

Figure 22:
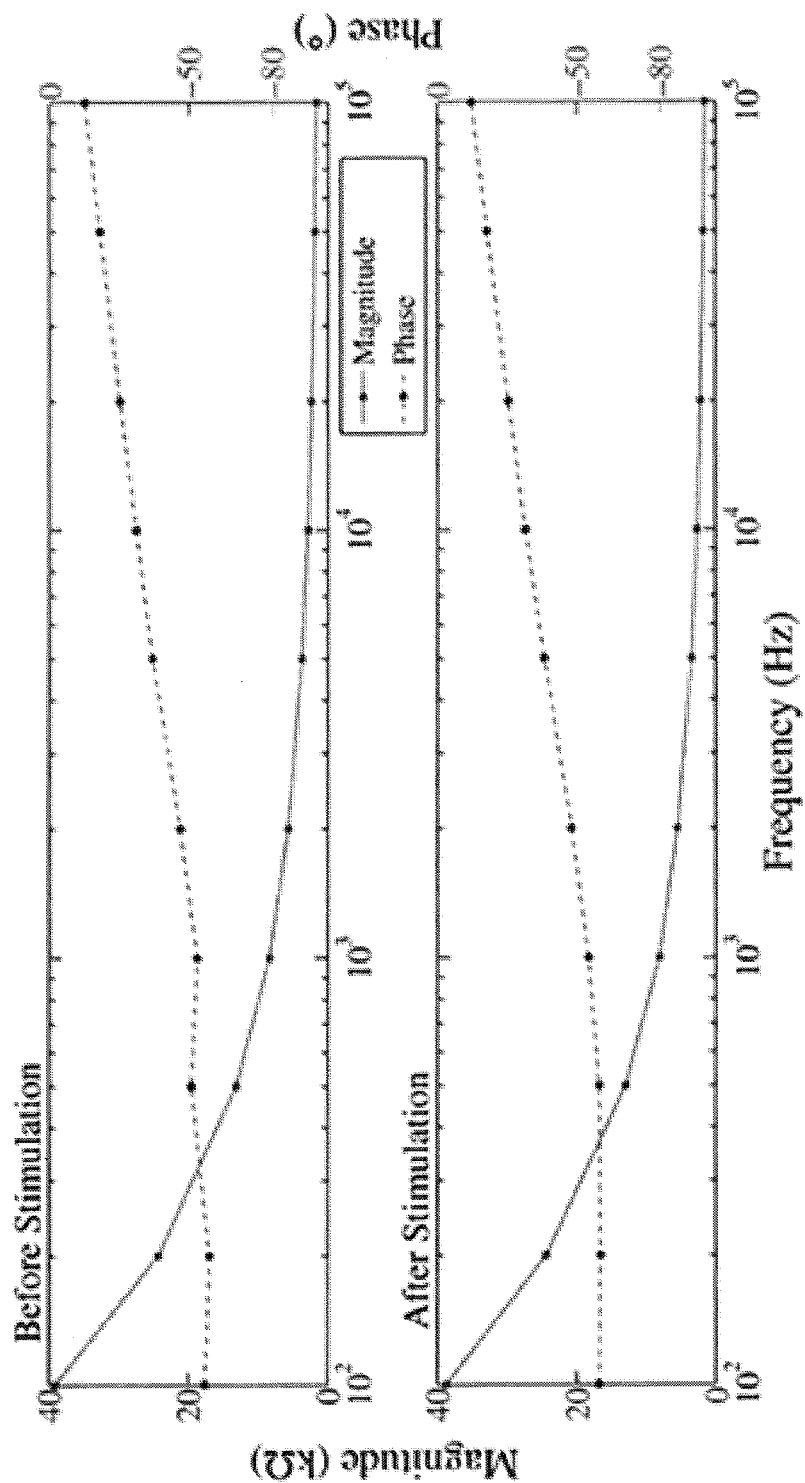
FIG. 22 shows stimulation electrode impedance before and after five minutes of continuous stimulation, consistent with various aspects of the present disclosure.

FIG. 22 shows stimulation electrode impedance before and after five minutes of continuous stimulation, consistent with various aspects of the present disclosure. Possibly due to a decrease in electrode impedances with increasing frequencies (FIG. 22), the electrode voltages were significantly reduced with high frequency stimulation compared to single pulses. The decrease in voltage was especially significant in mid-range frequencies (75 Hz–5 kHz), reaching four-fold reduction at 2.5 kHz compared to single pulse (1.39±0.26 $V_{p-p}$ for single pulse versus 0.34±0.074 $V_{p-p}$ for 2.5 kHz burst, p<0.001). At higher frequencies (>12.5 kHz), the decrease in voltages was not as significant, as the increase in current thresholds becomes larger than the decrease in impedance. As a result of the reduced voltages, frequencies in the 75 Hz–2.5 kHz range led to lower power requirements (current×voltage) for excitation of the cells, despite the higher current thresholds.

Strength-Duration (S/D) curves for high frequency stimulation were also determined for burst durations from 5 to 80 ms. The number of biphasic pulses tested at each duration ranged from 1 (equivalent to a single biphasic pulse) to 1000.

Figure 23:
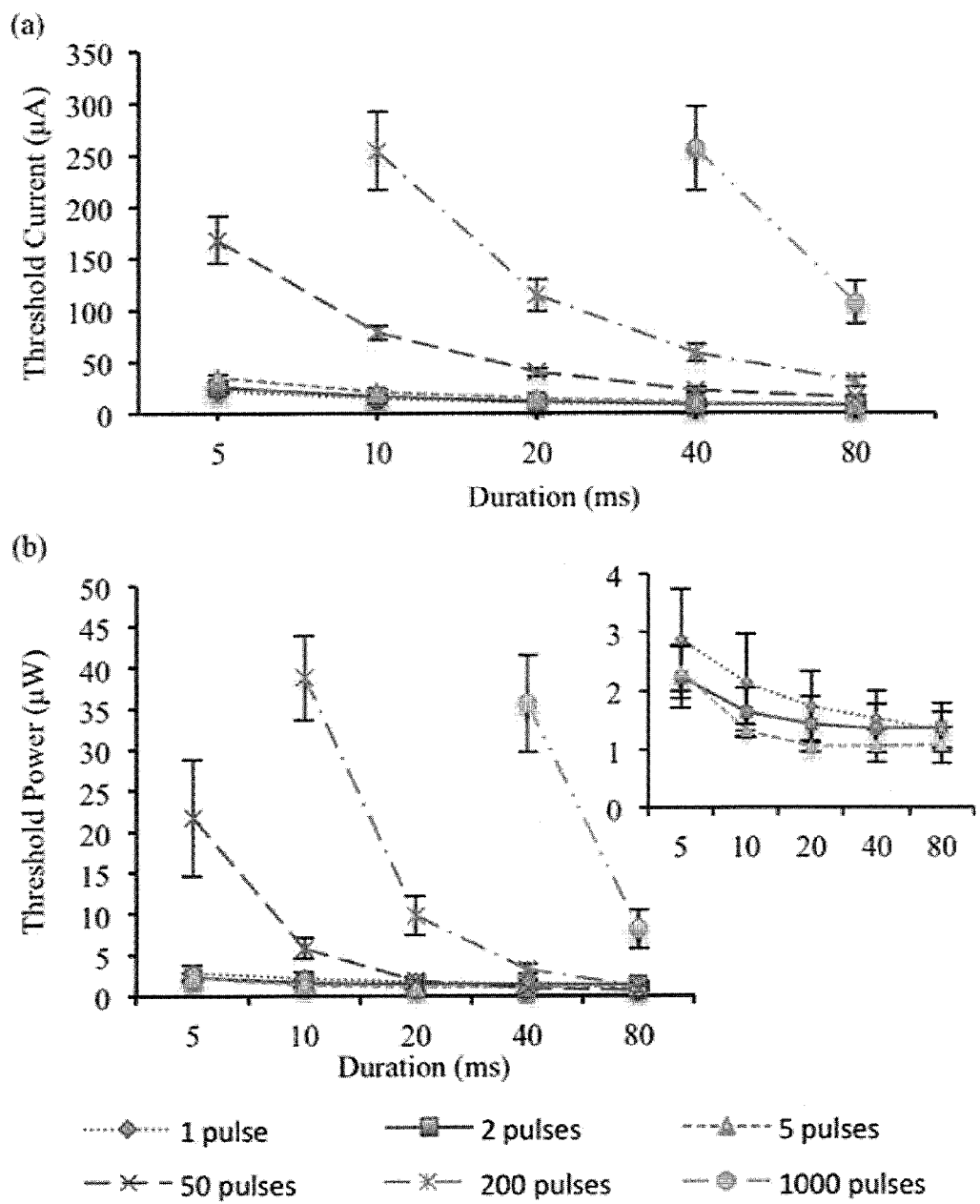
FIG. 23A shows curves for current thresholds at increasing stimulus burst pulse count (increasing frequencies), consistent with various aspects of the present disclosure.
FIG. 23B shows curves for power thresholds at increasing stimulus burst pulse count (increasing frequencies), consistent with various aspects of the present disclosure.

FIG. 23A shows curves for current thresholds at increasing stimulus burst pulse count (increasing frequencies), consistent with various aspects of the present disclosure, and FIG. 23B shows curves for power thresholds at increasing stimulus burst pulse count (increasing frequencies), consistent with various aspects of the present disclosure. As expected, shorter duration bursts required higher currents as shown in FIG. 23A. The trend was more pronounced for bursts with higher pulse counts, with some not even able to trigger depolarization below some duration (10 ms for 200 pulses, 40 ms for 1000 pulses). Current threshold S/D curves for multiple-pulse bursts (FIG. 23A) were higher than that of a single biphasic pulse. Increasing the burst duration at the same stimuli frequency led to reduction in required current amplitude (from $I_{p-p}$=39.6±3.91 pA at 50 pulses in 20 ms to $I_{p-p}$=30±5.14 pA at 200 pulses in 80 ms, corresponding frequency 2.5 kHz, FIG. 23) along with concomitant reduction in electrode potential (from $V_{p-p}$=0.39±0.09 pA at 50 pulses in 20 ms to $V_{p-p}$=0.30±0.06 pA at 200 pulses in 80 ms, corresponding frequency 2.5 kHz). As revealed by the S/D curves for power thresholds (FIG. 23B), bursts with low pulse count actually led to reduced power requirements, with two and five pulses outperforming on average the single pulse for all durations (although statistical significance was not reached).

Visual inspection of the stimulation electrodes under microscope did not reveal any sign of corrosion or other structural damage under stimulation conditions reflecting the protocols used in this study (200 $\mu A_{p-p}$, 5 kHz, 20 ms burst duration, 1 Hz repetition, 5 minute continuous stimulation, no cell plated).

Artifact reduction with high frequency stimulation was successfully demonstrated. In contrast to single biphasic pulses which saturated the amplifiers (±5V rails) even beyond the stimulus duration, high frequency bursts did not cause such saturation. Artifacts were reduced to levels comparable to the AP. The much larger peak-to-peak values compared to RMS value reflect the sharp onset and offset of the artifact. In addition, the time for the artifact to return to baseline level (recovery time) was reduced to a few milliseconds. Note that the larger peak-to-peak amplitude of artifacts obtained at 10 kHz compared to the ones at 5 kHz reflects the higher currents necessary to capture the tissue at that frequency.

Shaping of the burst envelope further attenuated the remaining artifact. A simple triangular envelope was optimized experimentally to both reduce the artifact and decrease its recovery time. Best results were found with an asymmetrical wave, one-third ramping up and two-third ramping down. The peak amplitude of the stimulus bursts had to be increased typically by 30 to 50% to maintain capture (reflecting a conservation of the RMS value). Despite this, the artifacts were significantly reduced compared to rectangular bursts, in particular with respect to the high frequency onset and offset present in the rectangular bursts and affecting the peak-to-peak value of the artifacts. Overall, this burst shaping approach brought the artifact to levels lower than typical recorded action potentials.

The substantial mitigation of the artifacts also brought about the ability to detect the action potentials during stimulation. With the artifact smaller than the AP, superposition of both only brings minor distortions to the shape of the recorded AP. The distortion is more pronounced in the case of the 10 kHz stimulation due to the higher current threshold. However, for both stimulation frequencies, the APs were clearly visible, and amenable to timing extraction.

Simulations revealed higher current thresholds with increasing frequencies (from $I_{p-p}$=190 pA at 25 Hz to $I_{p-p}$=42 nA at 5 kHz for 40 ms, cathodic-first bursts), as observed in experiments. Simulations also predicted higher thresholds for bursts with initial anodic phase compared to cathodic ones ($I_{p-p}$=52 nA for anodic-first, $I_{p-p}$=42 nA for cathodic-first, at 5 kHz). In addition, the mechanism of excitation was also dependent on the initial phase of the bursts, as revealed in FIG. 24 for a 40 ms, 2.5 kHz stimulus applied at t=10 ms. More specifically, FIGS. 24A-24P show example single cell simulation results for a high frequency stimuli at 2.5 kHz for anodic-first and cathodic-first burst, delivered between t=10 ms and t=50 ms (insets detail the response between t=43 ms and t=45 ms). High frequency stimuli increase membrane potential (as shown in FIGS. 24A and 24I) until the threshold by accumulation of positive ions inside the cell by activation of inward rectifier potassium channel (as shown in FIG. 24F) and sodium channel (as shown in FIG. 24J) for anodic-first and cathodic-first bursts respectively, consistent with various aspects of the present disclosure.

Figures 24A, 24B, 24C, 24D, 24E, 24F, 24G, 24H:
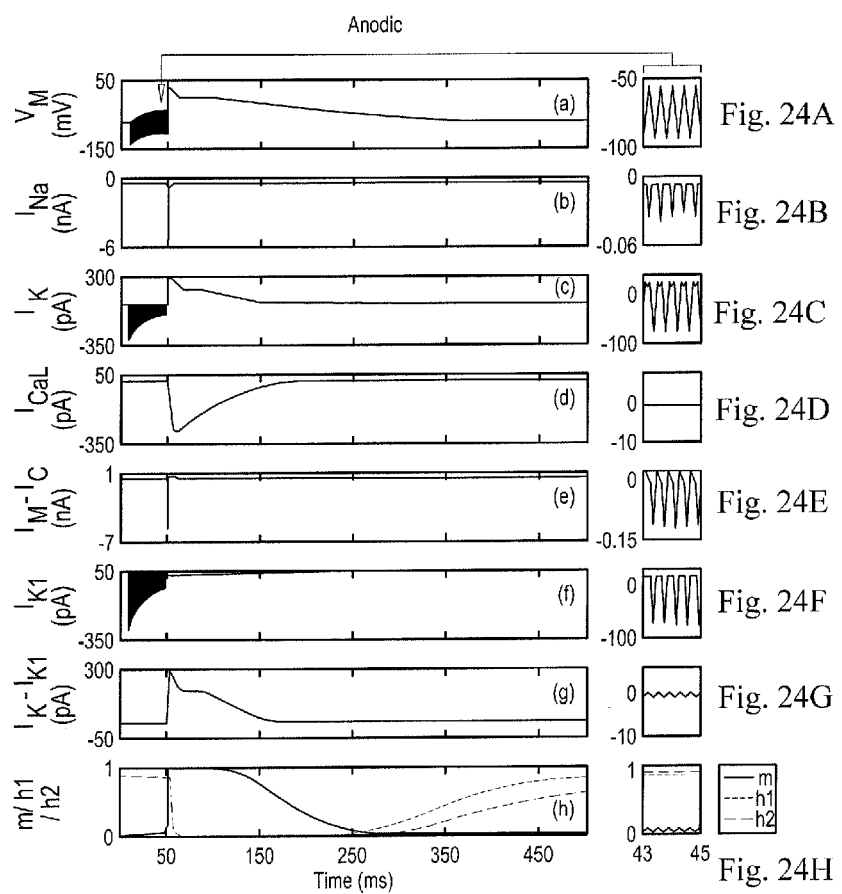
FIGS. 24A-24H show example single cell simulation results for a high frequency stimuli at 2.5 kHz for anodic-first and cathodic-first burst, consistent with various aspects of the present disclosure, wherein each of FIGS. 24A, 24B, 24C, 24D, 24E, 24F, 24G, and 24H shows one such example.
Figures 24I, 24J, 24K, 24L, 24M, 24N, 24O, 24P:
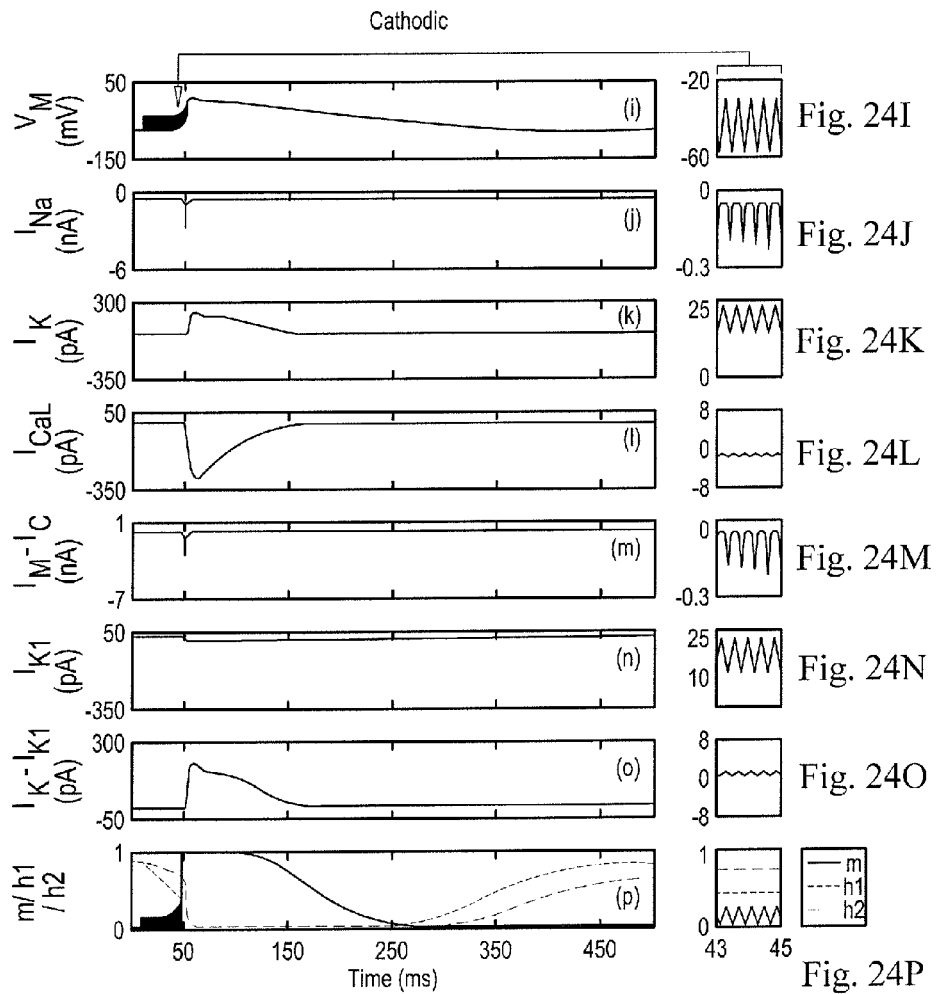
FIGS. 24I-24P show further example single cell simulation results for a high frequency stimuli at 2.5 kHz for anodic-first and cathodic-first burst, consistent with various aspects of the present disclosure, wherein each of FIGS. 24I, 24J, 24K, 24L, 24M, 24N, 24O, and 24P shows one such example.

For anodic-first bursts, the membrane voltage was driven to a more negative value on the initial phase (FIG. 24A), and activated the inward rectifier potassium channels ($I_{-K1}$, FIG. 24F). These channels allow inward $K^+$ flow when the membrane is hyper-polarized; hence they work to bring the voltage to its resting level. With the initial anodic phase, these channels were opened and pushed $K^+$ ions inside to counteract the stimulus. The following cathodic phase closed back these channels, but failed to reverse the effect of the first phase, as some $K^+$ ions accumulated inside during the anodic phase. As a result, overall effect of the first two phases was to increase membrane voltage. With the following phases, the channels repeated the cycle, accumulating more charges inside until the threshold was reached and an action potential was generated (FIGS. 24A and 24H). Other channels were not active during the stimulus (FIGS. 24B, 24D, and 24G). The excitation thus is driven mainly by $I_{-K1}$ channels.

For cathodic-first bursts, the initial phase resulted in a direct increase in membrane potential (FIG. 24I), but not large enough to generate an action potential. However, that increase activated the some of the $Na^+$ channels resulting in a net charge transfer (FIG. 24J). With the next anodic phase, these channels were closed but the effect of the first phase was not reverted completely due to prior accumulation of $Na^+$ inside. Consequently, an increase in membrane voltage resulted from these two phases. Following cycles led to the same response, incrementally raising the membrane potential until the threshold was reached and action potential was generated (FIGS. 24I and 24P). Other channels did not seem to contribute significantly (FIGS. 24K and 24L).

Overall, although bursts may not have stimulated by direct charge delivery due to their AC nature, they resulted in an active membrane response leading to rectification and accumulation of positive ions inside the cell. The type of ion involved was dependent on the leading phase of the stimuli. Accumulated charges increased the membrane potential until the voltage-activated sodium channel threshold (around −45 mV for the single cell model) was reached, ultimately generating an action potential. The rectification of stimulation currents is apparent in the plots of total membrane currents minus capacitive currents (which have a net sum close to zero), $I_M$-$I_C$ (FIGS. 24E and 24M), where incremental, monophasic pulses are visible.

In certain embodiments, the reduction of metal electrode impedance with frequency resulted in a significant reduction (up to four-fold) in threshold electrode voltages was observed with bursts of high frequency stimuli, compared to single pulses of same durations. Voltages were especially reduced in the mid-frequency range. At higher frequencies, the reduction became less significant as the increase in current thresholds exceeded the reduction in impedance. These results are of particular significance as one critical constraint of electrical stimulation is to maintain the electrode potential within a range that limits irreversible electrochemical reactions. These reactions can be material-dependant (corrosion, dissolution), but also include the hydrolysis of water, typically occurring beyond −0.6 V or +0.9V vs SCE. These irreversible reactions can result in production of cytotoxic compounds and alteration of local pH, possibly leading to electrode degradation and tissue damage. Increasing the magnitude and duration of the stimuli escalates these issues. This is also true for cardiomyocyte stimulation, which generally requires higher charges compared to neuron. In this case, the reduction in voltages obtained by high frequency stimulations could be used to lower the probability of irreversible reactions, and therefore improve the safety of stimulation. The reduction in stimulation voltage achieved here is believed to be caused, at least in part, by the reduction in electrode impedance. However, results show that increasing burst duration can further reduce these voltages.

From a power perspective, frequencies between 75 Hz and 2.5 kHz lead to slightly lower requirements for excitation of the cells, despite higher current thresholds, and this is believed to be due to the reduced electrode impedances and voltages in these frequencies. This can be useful for energy-efficient stimulation devices. In addition to the power delivered to cells at the electrode ($I_{Th} \cdot V_{Electrode}$), and account the power drawn from the power supply ($I_{Th} \cdot V_{Supply}$, $V_{Supply} > V_{Electrode}$) can also be accounted for.

Figure 25:
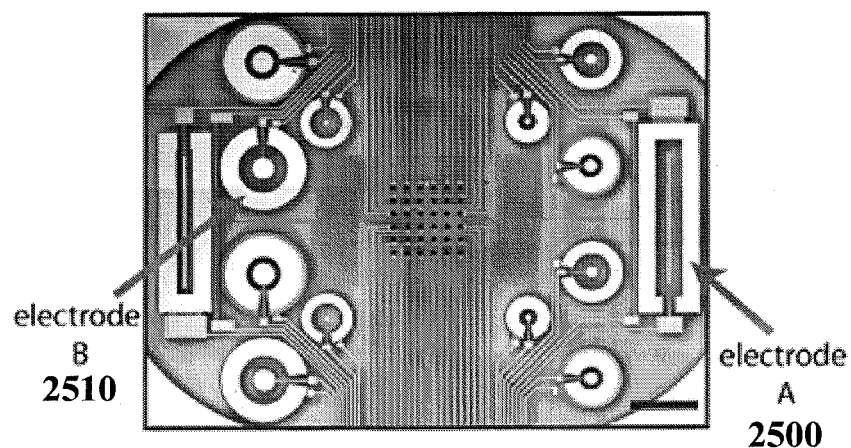
FIG. 25 shows an example microelectrode array, consistent with various aspects of the present disclosure.

Using a microelectrode array, as shown in FIG. 25, HL-1 cardiomyocytes, a mouse-derived atrial cell line, were stimulated, and the electrical activity thereof was recorded. Simultaneous $Ca^{2+}$ imaging was performed to map the response of the cells to electrical stimulation. The effects of AC stimulation were determined indiscriminately in spontaneously beating cultures or paced cultures (if not spontaneously beating). In the latter case, one of the large stimulation electrodes 2500 on each side of the array was used for pacing. Beating rates ranged between 60 and 120 beats per minute (bpm). For the investigation of stimulation parameters, current stimulation through an annular electrode 2510 (electrode B; area 0.2 mm²) was used in the experiments. The stimulations were carried out at eight distinct frequencies distributed between 50 Hz and 10 kHz using both square and sinusoidal waveforms. At each frequency, the peak-to-peak amplitude was increased in 1 to 5 µA steps beginning from 1 µA (corresponding current density 5 µA/mm²) until inhibition was observed. At low frequencies (50-100 Hz), a bimodal response from the tissue was observed. At low amplitudes, AC stimuli evoked multiple irregular extra beats (4 out of 6 cultures), often resulting in the disruption of the normal pacing activity or a change in the origin of the wavefront (pacemaker site). At higher amplitudes, a single action potential (AP) was generated, after which the electrical activity was suppressed without influencing the spontaneous activity in the non-stimulated areas. The irregular extra beats generated before reaching suppression thresholds could explain the induction of VF, multiple APs and hemodynamic collapse without inhibition.

Figure 26:
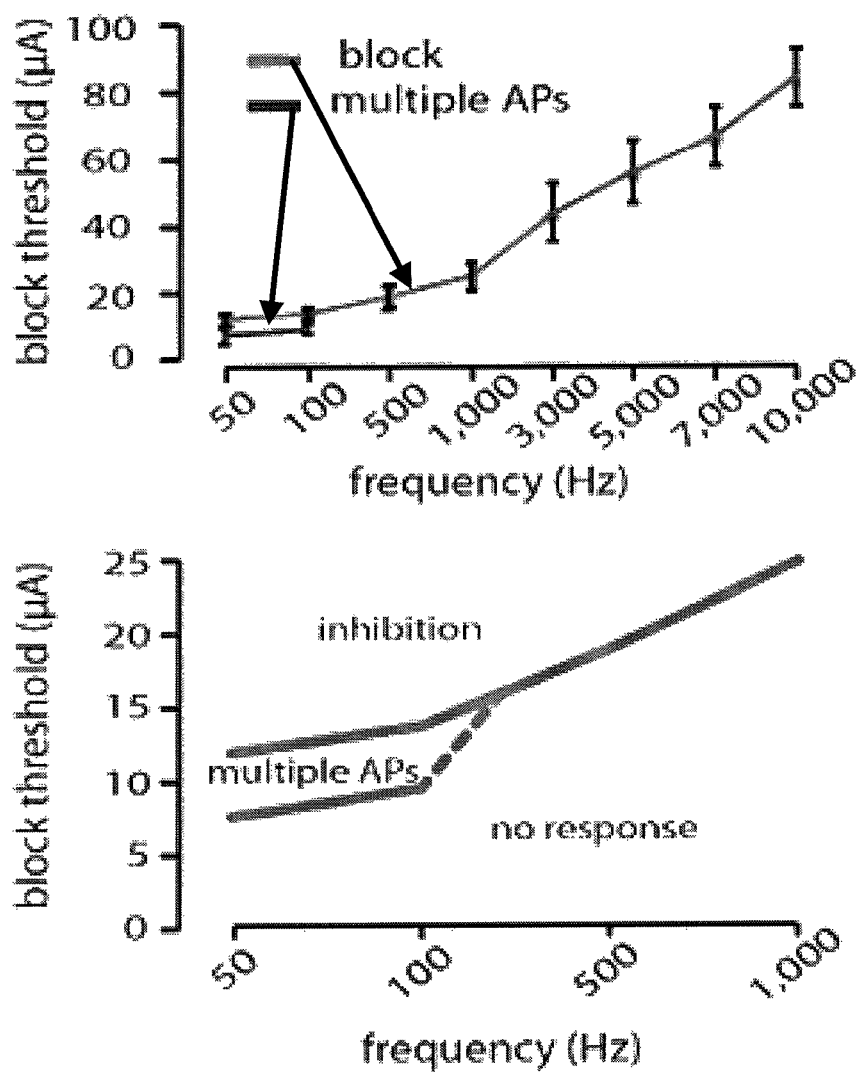
FIG. 26 shows an example relationship between blocking threshold and frequency, the bottom graph displays a close up (based on the top graph) of the cell response to low frequency AC stimuli, highlighting the region of entrainment (multiple APs) before full response is reached, consistent with various aspects of the present disclosure.
Figure 27:
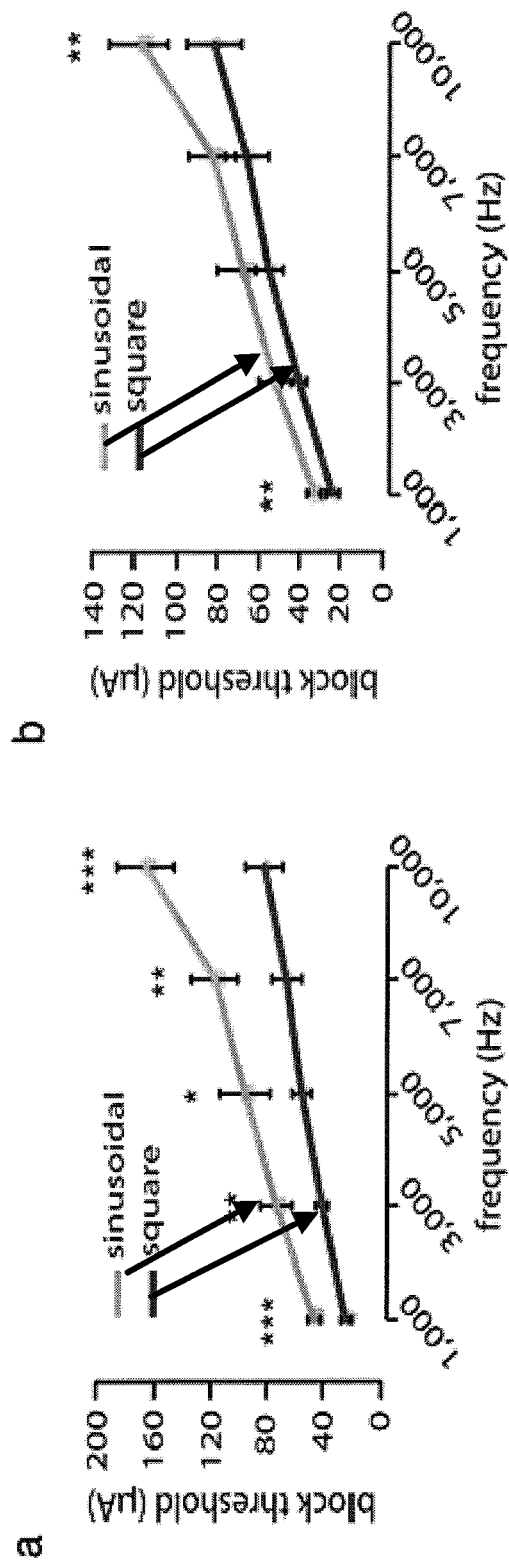
FIG. 27 shows an example comparison of inhibition thresholds between sinusoidal and square waveforms, consistent with various aspects of the present disclosure.

However, at higher frequencies (>100 Hz), AC stimuli surprisingly did not induce multiple extra beats, and generated suppression of the electrical activity after a single AP (6 out of 6 cultures, top graph of FIG. 26). This single AP did not cause a shift of the pacemaker sites or more than one skipped beat in paced cultures (due to the asynchronous onset of the inhibition stimulus). The reliability and controllability of the block were tested using varying electrode sizes (from 0.06 to 0.4 mm²) and stimuli durations (from 5 s to 300 s). The block was systemically induced and maintained in the cells overlying the electrodes for the duration of the stimulus (n>50 cultures). The block had rapid onset (within a beat; n>50) and rapid reversibility (within a beat; n>50) and was sustainable for long durations (tested up to 5 minutes; n=7 cultures). The spatiotemporal control was demonstrated with a large electrode enclosing a rectangular area, momentarily blocking the depolarization wave and preventing it from reaching and depolarizing the inner region. Further characterization showed an increase in inhibition threshold with increasing AC stimulation frequency (top graph of FIG. 26). Square waveforms required smaller amplitudes on average for suppression of activity compared to sinusoidal waveforms (even considering RMS values), although statistical significance was not reached for all frequencies (FIG. 27). FIG. 27 shows an example comparison of inhibition thresholds between sinusoidal and square waveforms, (a) peak-to-peak amplitudes; and (b) RMS amplitudes, statistical significance is not reached between f=3,000 and f=7,000 Hz (a, b; Error bars, s.d.; n=6 cultures; µA, microamperes; * indicate p<0.05;  indicate p<0.01; * indicate p<0.001). Overall, the combination of suprathreshold amplitudes and high frequencies thus leads to an effective inhibition and a well-defined response of the cells. In particular, high frequencies avoid potential entrainment associated with amplitude gradients surrounding stimulation electrodes (bottom graph of FIG. 26).

Figure 28:
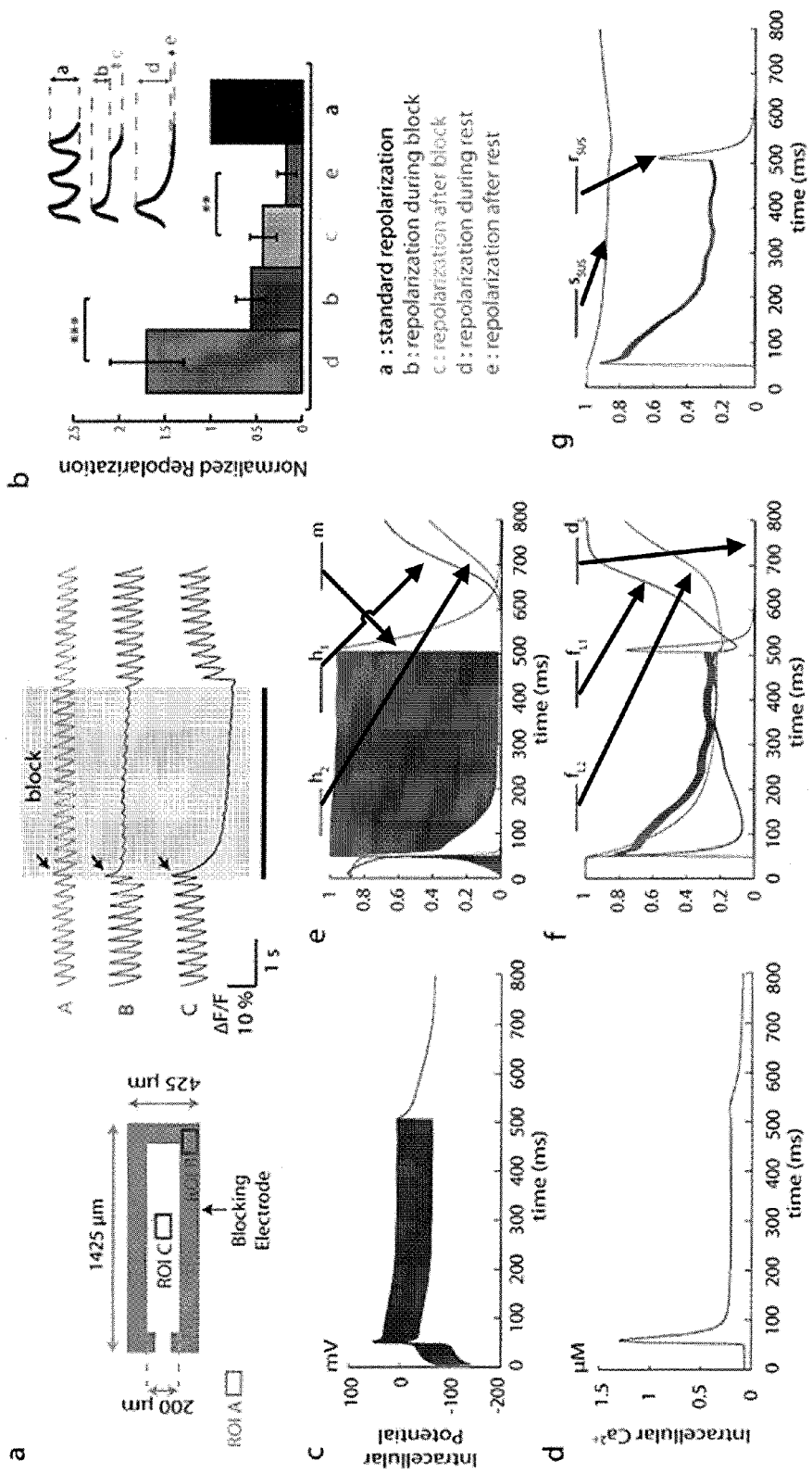
FIG. 28 (including respective FIGS. 28A-28G) shows example ionic mechanisms behind suprathreshold AC inhibition, consistent with various aspects of the present disclosure, wherein each of FIGS. 28A, 28B, 28C, 28D, 28E, 28F and 28G shows one such example.

To investigate the ionic mechanisms behind the high frequency block, cytosolic $Ca^{2+}$ dynamics were analyzed, and computer simulations were performed based on a single cell model. $Ca^{2+}$ imaging revealed that high frequency stimulation produced a single action potential followed by prolonged depolarization throughout the stimuli duration. FIG. 28 shows example ionic mechanisms behind suprathreshold AC inhibition. For instance, in FIG. 28A, the left portions display a representation of blocking electrode A with regions of interests (ROIs) for $Ca^{2+}$ imaging. The right portion of FIG. 28A shows an example of $Ca^{2+}$ recordings from ROIs during blocking experiments, arrows point to the action potential generated at onset of inhibition stimulus and the bar represents the inhibition duration. FIG. 28B shows repolarization analysis indicating prolonged action potentials for inhibited cells. Repolarizations are normalized with respect to standard repolarization during regular action potentials (Error bars, s.d.; n=9 cultures; * indicate p<0.001;  indicate p<0.01). In FIGS. 28A and 28B, the cells on the electrode surface showed prolonged elevated $Ca^{2+}$ levels while other regions outside the electrode showed typical action potential driven $Ca^{2+}$ transients, and the inhibited cells also prevented the electrical activity from reaching the cells inside the annular electrode. The prolonged depolarizations prevented the subsequent stimuli from depolarizing the tissue, hence producing local inhibition.

FIGS. 28C-F show single cell simulation results to 1 kHz square wave applied between t=10 ms and t=510 ms, prolonged action potentials revealed by (c) membrane potential and (d) intracellular $Ca^{2+}$ levels. More specifically, FIG. 28E shows inactivation of $Na^+$ channels (during the block, fast and slow inactivation gating parameters—$h_1$ and $h_2$—decreased to zero (activation gating variable m oscillated between 0 and 1)). Additionally, FIG. 28F shows prolonged activation of inward $Ca^{2+}$ channel (during the block, fast and slow inactivation gating parameters—$f_{L1}$ and $f_{L2}$—remained lowered while activation gating variable $d_L$ remained high compared to resting values). FIG. 28G shows prolonged activation of outward $K^+$ channel (during the block, inactivation gating variable $s_{SUS}$ lowered to 0.9 while activation gating variable $r_{SUS}$ plateaued around 0.3).

Figure 29:
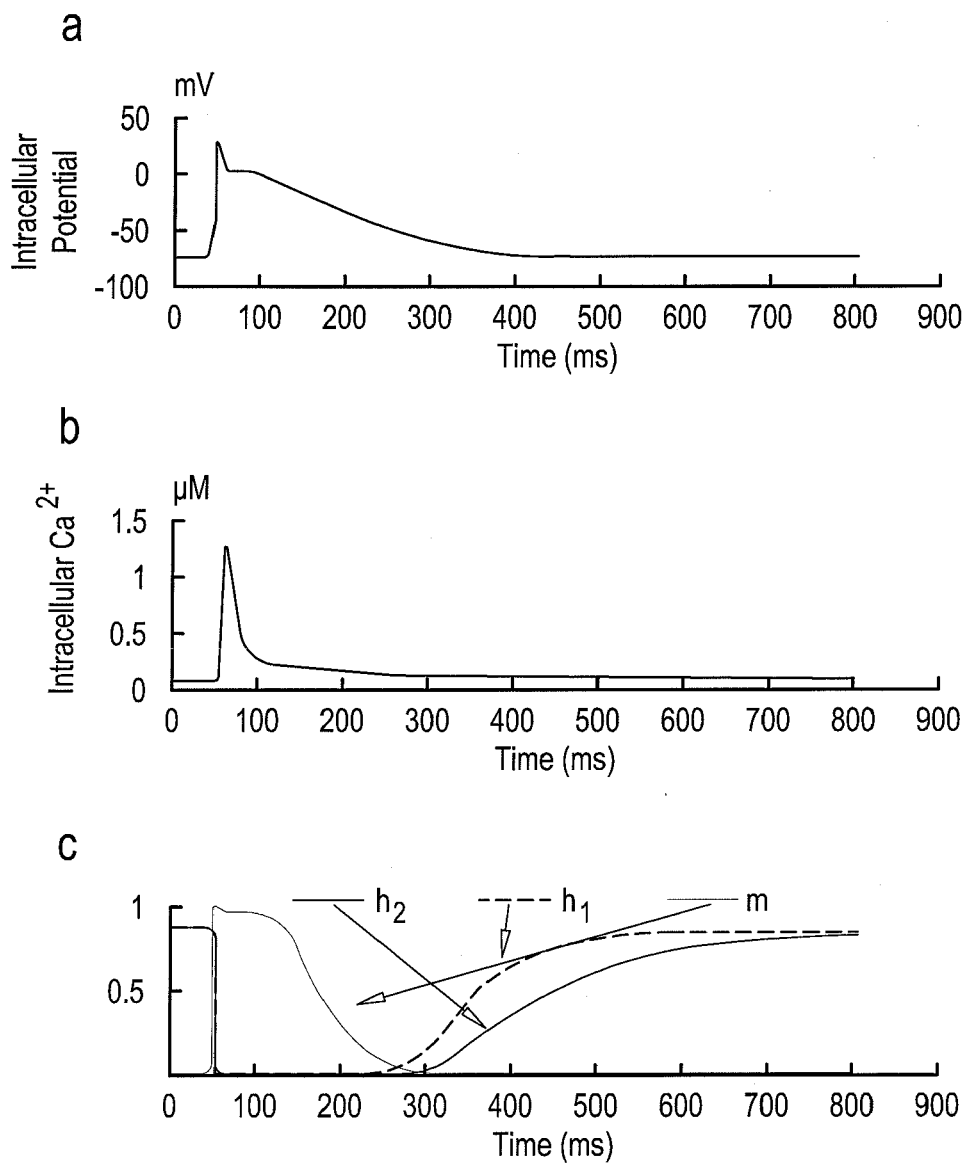
FIG. 29 (including respective FIGS. 29A-29E) shows single cell simulations displaying the results of an action potential, generated by a monophasic pulse, consistent with various aspects of the present disclosure, wherein each of FIGS. 29A, 29B, 29C, 29D and 29E shows one such example.

FIG. 29 shows single cell simulations displaying the results of an action potential generated by a monophasic pulse of 200 pA applied between t=40 and t=50 ms. FIG. 29A displays the membrane potential, FIG. 29B shows the intracellular $Ca^{2+}$ level, FIG. 29C shows the $Na^+$ channel activation and inactivation parameters, FIG. 29D shows the $K^+$ channel activation and inactivation parameters, and FIG. 29E $Ca^{2+}$ channel activation and inactivation parameters The single cell simulations reveal similar prolonged depolarizations and elevated $Ca^{2+}$ levels (e.g., as shown in FIGS. 28C-D and FIGS. 29A-B). At the membrane level, these simulations showed the inactivation of $Na^+$ channels (as shown in FIGS. 28E and 29C) and prolonged activation of $K^+$ and $Ca^{2+}$ channels (as shown in FIGS. 28F-G and FIGS. 29D-E) for the duration of the stimulus. The prolonged depolarization might thus be explained by the counteraction of the outward $K^+$ repolarization current by the inward $Ca^{2+}$ current—sustained for the duration of the stimuli—while the suppression of further depolarization might be related to the inactivated $Na^+$ channels.

Figure 30:
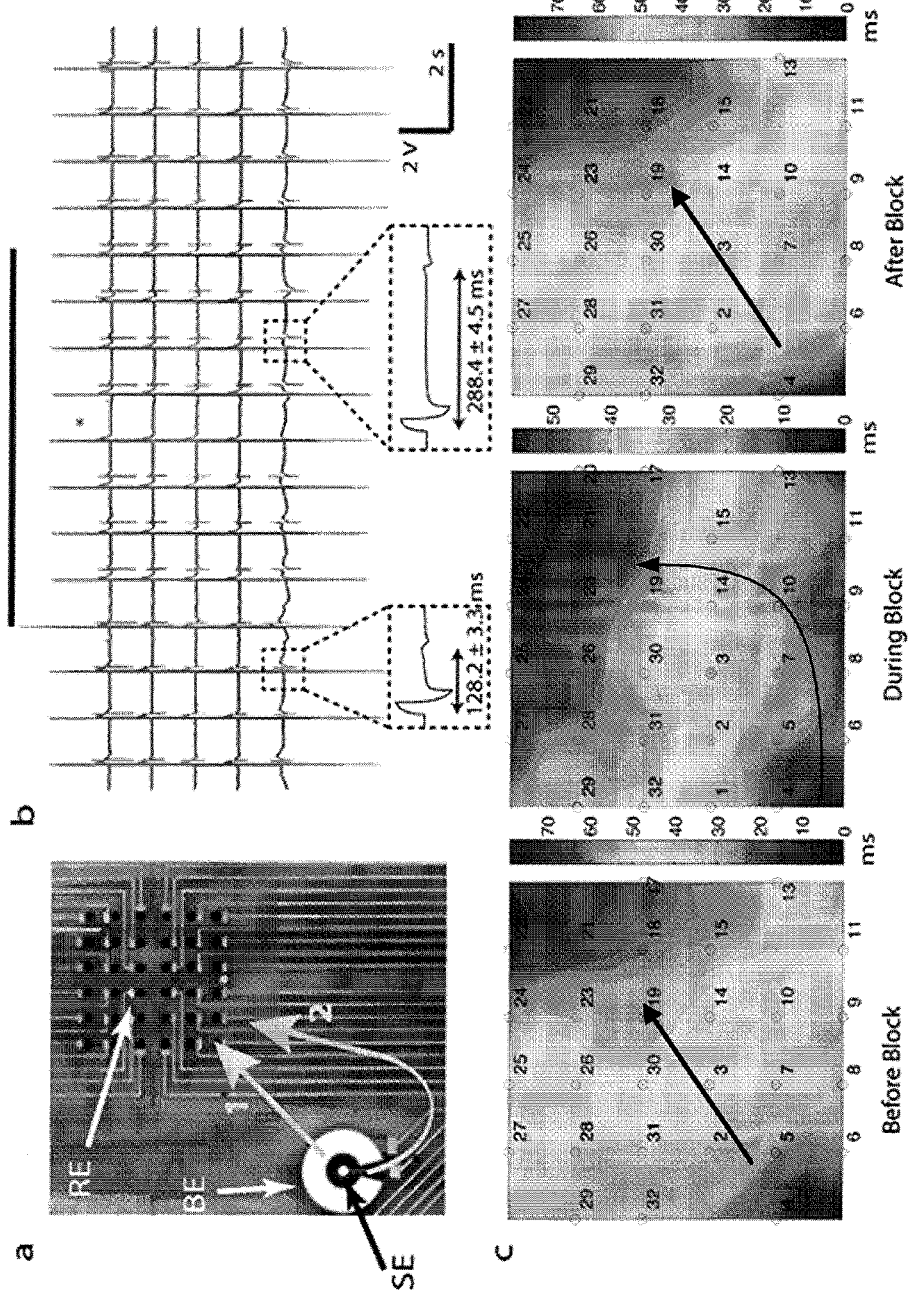
FIG. 30 (including respective FIGS. 30A-30C) shows an example guidance of a conduction path using high frequency suprathreshold AC stimuli, consistent with various aspects of the present disclosure, wherein each of FIGS. 30A, 30B and 30C shows one such example.

In addition to the spatiotemporal control of inhibition, certain embodiments of the present disclosure are directed toward controlling conduction path as an illustration of the potential for in vitro assays. The cardiomyocytes were paced using one of the stimulation electrodes at 60 bpm and blocking was performed with the surrounding incomplete annular electrode. FIG. 30 shows an example guidance of conduction path using high frequency suprathreshold AC stimuli. FIG. 30A shows the microelectrode array used in the experiment, with arrows labeled 1 and 2 representing the conduction paths before and during the block (as derived from the isochrone maps in FIG. 30C revealing the direction change in conduction path). SE denotes the stimulation electrode used for pacing cells, BE denotes the blocking electrode, and RE denotes recording electrodes. FIG. 30B shows the electrical recordings showing the change in conduction path during blocking by the increased time delay between stimulation pulse and LATs, lower bar represents the block duration (* denotes one missed beat during the experiment).

Blocking AC stimulation was performed at 5 kHz at the inhibition threshold amplitude. Without the blocking stimulus, evoked electrical activity spread radially from the pacing electrode to other regions. From electrical recordings, the initial propagation path was estimated using the local activation times (LATs) of the recorded action potentials (path labeled 1, FIGS. 30A and 30C). Upon turning on the blocking AC stimulus, the recordings showed increase in the average time delay (from 128.2±3.3 ms to 288.4±4.5 ms; n=4 beats) between the pacing pulse and average LATs on the recording electrodes (FIG. 30B). As determined by the isochrone maps, the initial propagation path was blocked and depolarization originating from the pacing electrode was propagated to other regions through the unblocked opening of the incomplete annular electrode (path labeled 2, FIGS. 30A and 30C). Termination of the blocking signal restored the propagation of activity in the initial path (FIGS. 30A-30C). The ability to pattern conduction pathways via the blocking mechanism presented could help generate in vitro models reproducibly replicating complex conduction patterns such as spiral and reentrant waveforms for the study of fibrillation.

The microelectrode arrays (MEA) used in the experimental embodiments and results included a 6×6 array of platinum electrodes with 22 µm diameters and a pitch of 100 µm. This arrangement also included additional larger electrodes on two sides for electrical stimulation. Petri dishes (35 mm diameter) with a 1 cm diameter through-hole were fixed to the package using an epoxy glue (EP42HT, Master Bond; Hackensack, N.J.). Signals from the MEA were amplified by a custom amplifier system with a two-stage gain of 60 dB, a 4 Hz first-order high-pass cut-off, and an eighth-order low-pass cutoff at either 1.5 or 3 kHz, as previously reported. 32 channels (four corner electrodes excluded) from the amplifier board were digitized with 12-bit resolution at 10 ksps and acquired by a custom designed visualization and extraction tool, written in Matlab™.

Isochrone maps were used to analyze conduction patterns. These maps were constructed based on the position and local activation time (LAT) of each electrode. LATs were defined as the point of maximum negative slope of an extracellular action potential (minimum of the derivative).

The HL-1 cell line (Louisiana State University Health Science Center, New Orleans, La., USA), derived from mouse atrial myocytes, was used in all described experiments. Cells were cultured in T25 flasks at 37° C. and 5% $CO_2$ in culture medium consisting of Claycomb media (Sigma, St. Louis, Mo., USA), supplemented with 10% fetal bovine serum (Invitrogen, Carlsbad, Calif., USA), 100 μM norepinephrine (Sigma), 100 units/ml penicillin-streptomycin (Invitrogen), and 4 mM L-glutamine (Invitrogen) in a humidified chamber. After cells reached confluency and started beating, they were seeded onto microelectrode arrays as described previously. Briefly, prior to seeding the cells, the microelectrode arrays were sterilized with 70% ethanol, rinsed with PBS (pH 7.2, Invitrogen), and coated with an adhesion-promoting solution containing 12.5 μg/ml fibronectin (Sigma) and 0.02% gelatin (VWR, Radnor, Pa., USA) and stored in a 37° C. incubator overnight. Cells were rinsed with PBS then trypsinized using 1.5 mL 0.05% trypsin/EDTA (Invitrogen) in incubator for 10 min. Trypsinization was stopped by adding 4.5 mL of medium followed by centrifugation (5 min, 1000 g). Supernatant was removed and the pellet was re-suspended in 5 mL media. The gelatin/fibronectin solution was aspirated from the arrays and replaced with 50-100 μL cell suspension. After one hour of settling time, chips were filled with 2 mL of medium. Medium was changed daily. Experiments were performed after cells reached confluency, usually 2-4 days after plating. The cultures were viable until 7-10 days following plating, depending upon plating density.

Blocking experiments were performed as described consistent with the above. Cultures not showing spontaneous beating were paced using biphasic pulses at 60 bpm. Further, in experiments evaluating the reliability and controllability, square waveform blocking stimulus at 5 kHz was used. In all experiments, current-controlled stimulation was performed using a custom-made voltage-controlled current source.

In $Ca^{2+}$ imaging, cells were incubated with a 1:1 mixture of Fluo-4 Direct™ (Invitrogen) and culture medium at 37° C. for 30 min. The mixture was aspirated and replaced with 1 ml culture medium before measurements. Calcium activity was recorded on an upright microscope (Olympus BX60M) with ×10 objective. Fluo-4 was excited using a mercury lamp through a 450-480 nm bandpass excitation filter. Fluorescence was collected through a high-pass emission filter at 515 nm. Frames were collected using a cooled CCD camera (Retiga-2000R, QImaging, Surrey, BC, Canada) at 20 Hz using QCapture Software (QImaging). Regions of interest (ROI) were selected where brightness changed significantly with contractions. Calcium changes were detected in the three ROIs indicated (FIG. 28A; in, on and outside the blocking electrode) and expressed as the fluorescent intensity ratio $\Delta F/F = (F-F_0)/F_0$, in which F is the fluorescence and $F_0$ is the minimum fluorescence detected during a typical action potential. For time-lapse images, each pixel was normalized to the maximum range of fluorescence measured during normal beating. Noise in each frame (300×400 pixels) was then removed using a 10×10 median filter. For the supplementary movie, a 6×6 median filter was used instead in order to preserve more details.

In single cell simulations, a mathematical model of the human atrial myocyte was used for the single cell simulations. The model was based on averaged voltage-clamp data recorded from isolated single myocytes and composed of fluid compartment model including intracellular, cleft and extracellular spaces. It accounted for the changes in ionic concentrations in the cytoplasm as well as in the sarcoplasmic reticulum. The behavior of the cell was investigated under the case of transmembrane stimulation. Stimulations were simulated at 1 kHz at inhibition threshold amplitude using a square AC waveform of 0.5 second duration. Typical simulation duration was chosen as 0.8 second to allow repolarization of the cell after the stimulus.

Statistical data are shown as mean±s.d. For analysis of significance, paired Student's t-test (repolarization analysis) was used and a $p < 0.05$ was considered statistically significant. Significances were indicated with three stars for $p < 0.001$ and two stars for $p < 0.01$. The n values in the text and legends indicate the number of independent experiments (HL-1 cultures).

Mechanisms by which single pulses generate depolarizations using high frequency stimulation are surprising, as effects of the cathodic phase would typically be cancelled by the following anodic phase according to basic understanding of slower biphasic pulse stimulation. The single-cell simulations point to a rectification mechanism at the membrane level leading to accumulation of charges inside the cell. Such integration was similarly demonstrated for neurons, and inward rectification by $Na^+$ channels has been shown as the underlying mechanism. Additionally, a slight anomalous inward rectification of $K^+$ channels has been observed, as indicated by the experiments in tetraethylammnium chloride.

For cardiac cells, a rectification by sodium or potassium channels is dependent on the leading phase of the stimulation. Simulations also revealed higher thresholds for anodic-first bursts compared to cathodic-first. This type of behavior is characterized for single pulses; however, the experimental embodiments discussed in detail herein did not exhibit the same behavior. One possible explanation for this discrepancy is the lack of time-dependence of the inward rectifier $K^+$ channels in the model used, justified by the very short time-constant measured experimentally (sub-millisecond). Although this would not affect simulations of low frequency stimulus, it might lead to a misestimation of $I_{K1}$ currents in high frequency stimuli. Given that the experiments revealed similar thresholds independently of the leading phase of the stimuli, it is likely that inward rectification by $Na^+$ channels is the single dominant basis for high frequency stimulations in cardiac cells. This would also be supported by the experiments in which the leading phase was not controlled. Additionally, single-cell simulations do not take into account the effects of electrical gradients and virtual electrode polarizations (VEPs), usually present in extracellular stimulation of a syncitium, and possibly affecting the thresholds.

Various experimental embodiments of high frequency electrical stimulation of cardiac cells relying on bursts of square wave stimulation reliably capture and pace HL-1 cardiomyocytes. Stimulation parameters—strength/duration curves, current thresholds—were analyzed and results were compared to single biphasic stimuli. The mechanisms behind this type of stimulation were investigated with single-cell computer models, and simulations suggested a channel-specific response based on the rectification of the AC stimulus at the membrane level.

From an electrochemical standpoint, the lower potential thresholds resulting of high frequency stimulation can be beneficial in reducing the probability of irreversible electrochemical reactions and associated tissue damage. This may have a significant impact for long-term stimulation. From a power standpoint, it was found that stimulation within a range of frequencies can actually require less power compared to biphasic pulses, although this result was not statistically significant. Additionally, the stimulation artifacts caused by this type of stimulation can be largely separated in the frequency domain, leading to residual artifacts of lower amplitude than the action or field potentials. This stimulation technique can readily be integrated into commercial stimulators, MEA systems, pacemakers and other electrophysiology devices (e.g., cardiac mapping devices, RF ablation equipment).

TABLE 1

Input-Referred Amplitudes Of High frequency Stimulation Artifacts, For Various Stimulation Frequencies, Amplification Bandwidths And Burst Shapes (Avg ± Sd, N = 7 Cultures)

|  | 5 kHz Stimulus (BW 0.67-1.5 kHz) | | 10 kHz Stimulus (BW 0.67-3 kHz) | |
| --- | --- | --- | --- | --- |
|  | Rectangular (mV) | Triangular (mV) | Rectangular (mV) | Triangular (mV) |
| Peak-to-peak | 2.88 ± 1.53 | 0.25 ± 0.18 | 3.37 ± 2.10 | 0.55 ± 0.26 |
| RMS | 0.79 ± 0.39 | 0.19 ± 0.14 | 0.72 ± 0.30 | 0.42 ± 0.21 |

TABLE 2

Explanation of Symbols

| Symbol | Explanation |
| --- | --- |
| $V_M$ | Membrane potential |
| $I_{Na}$ | Sodium current |
| $I_K$ | Total potassium current |
| $I_{CaL}$ | L-type calcium current |
| $I_M$ | Total membrane current |
| $I_C$ | Capacitive component of the membrane current |
| $I_M$-$I_C$ | Total membrane current excluding capacitive component |
| $I_{K1}$ | Inwardly rectifier potassium current |
| $I_K$-$I_{K1}$ | Total potassium current excluding inwardly rectifier current |
| m | Activation gating variable for $I_{Na}$ |
| h1 | Fast inactivation gating variable for $I_{Na}$ |
| h2 | Slow inactivation gating variable for $I_{Na}$ |

The embodiments and specific applications discussed herein may be implemented in connection with one or more of the above-described aspects, embodiments and implementations, as well as with those shown in the U.S. Provisional Patent Applications, Ser. No. 61/543,103 filed on Oct. 4, 2011, of Ser. No. 61/543,115 filed on Oct. 4, 2011, and of Ser. No. 61/543,125 filed on Oct. 4, 2011; each of these patent documents, and the Appendices filed in the underlying provisional applications, including the references cited therein, are fully incorporated herein by reference. Consistent therewith, various embodiments discussed herein can be used alone or in combination with one another and/or with the teachings of these patent documents.

It is recognized that aspects of the disclosure can be practiced with circuits and computer/processor-based system configurations other than those expressly described herein. The corresponding structure for a variety of these systems and circuits would be apparent from the intended application and the above description.

The various terms and techniques are used by those knowledgeable in the art to describe aspects relating to one or more of communications, protocols, applications, implementations, and mechanisms. One such technique is the description of an implementation of a technique expressed in terms of an algorithm or mathematical expression. While such techniques may be implemented, for example, by executing code on a computer processor, the expression of that technique may be conveyed and communicated as a formula, algorithm, or mathematical expression.

For example, a block or module denoting "C=A+B" as an additive function implemented in hardware and/or software would take two inputs (A and B) and produce a summation output (C), such as in combinatorial logic circuitry. Thus, the use of formula, algorithm, or mathematical expression as descriptions is to be understood as having a physical embodiment in at least hardware (such as a processor circuit in which the techniques of the present disclosure may be practiced as well as implemented as an embodiment).

In certain embodiments, machine-executable instructions are stored for execution in a manner consistent with one or more of the methods of the present disclosure. The instructions can be used to cause a general-purpose or special-purpose processor that is programmed with the instructions to perform the steps of various methods. The steps may be performed by specific hardware components that contain hardwired logic for performing the steps, or by any combination of programmed computer components and custom hardware components.

In some embodiments, aspects of the present disclosure may be provided as a computer program product, which may include a machine or computer-readable medium having stored thereon instructions, which may be used to program a computer (or other electronic devices) to perform a process according to the present disclosure. Accordingly, the computer-readable medium includes any type of media/machine-readable medium suitable for storing electronic instructions.

Various modules may be implemented to carry out one or more of the operations and activities described herein and/or shown in the figures. In these contexts, a "module" is a circuit that carries out one or more of these or related operations/activities. For example, in certain of the above-discussed embodiments, one or more modules are discrete logic circuits or programmable logic circuits configured and arranged for implementing these operations/activities, as in the circuit modules/modes shown the various figures. In certain embodiments, the programmable circuit is one (or more) computer circuits programmed to execute a set (or sets) of instructions (and/or configuration data). The instructions (and/or configuration data) can be in the form of firmware or software stored in and accessible from a memory (circuit). As an example, first and second modules include a combination of a CPU hardware-based circuit and a set of instructions in the form of firmware, where the first module includes a first CPU hardware circuit with one set of instructions and the second module includes a second CPU hardware circuit with another set of instructions.

While the present disclosure is amenable to various modifications and alternative forms, specifics thereof have been shown by way of example in the drawings and will be described in further detail. It should be understood that the intention is not to limit the disclosure to the particular embodiments and/or applications described. On the contrary, the intention is to cover all modifications, equivalents, and alternatives falling within the spirit and scope of the present disclosure.

What is claimed is:

1. A device for controlling depolarization in cardiac cells in cardiac tissue, the device comprising:
   one or more circuits configured and arranged to
      generate an electrical stimulus in a frequency range exceeding 0.5 kHz and less than 500 kHz; and
      maintain the electrical stimulus over a period of time sufficient to inhibit action potentials in the cardiac cells and during the period of time, simultaneously detect whether the electrical stimulus has caused inhibition of action potentials in the cardiac cells by monitoring frequency components of an electrical signal coupled to the cardiac tissue while applying the electrical stimulus; and
   an electrode arrangement configured and arranged to
      deliver the electrical stimulus to cardiac cells and depolarize the cardiac cells.

2. The device of claim 1, wherein the one or more circuits are configured and arranged to maintain the electrical stimulus to inhibit action potentials in the cardiac cells subsequent to the depolarization thereof.

3. The device of claim 2, wherein the one or more circuits are configured and arranged to adjust the electrical stimulus in response to detecting a presence of action potentials in the cardiac cells caused by the electrical stimulus.

4. The device of claim 1, wherein the one or more circuits are configured and arranged to deliver the electrical stimulus in multiple bursts and, for each burst, to generate an action potential in the cardiac cells, and wherein the one or more circuits are further configured and arranged to record the action potential simultaneously while applying the electrical stimulus.

5. The device of claim 4, wherein the one or more circuits are configured and arranged to pace cardiac tissue by periodically repeating the burst.

6. The device of claim 1, wherein the one or more circuits are configured and arranged to inhibit action potentials by modifying the delivery of the electrical stimulus until an absence of an action potentials is detected in the cardiac cells.

7. The device of claim 1, wherein the electrical stimulus is between 1 kHz and 10 kHz.

8. The device of claim 1, wherein the electrical stimulus is a biphasic signal.

9. The device of claim 1, wherein the circuit is further configured and arranged to filter, from a measured electrical signal, stimulation-related high frequency components from cardiac tissue-related low frequency components and to monitor for action potentials in the filtered electrical signal.

10. The device of claim 9, wherein the electrode arrangement is a single electrode that both provides the electrical stimulus and receives the electrical signals from the cardiac cells.

11. The device of claim 1, wherein the electrode arrangement includes a plurality of electrodes and a control circuit for selectively delivering the electrical stimulus to the plurality of electrodes.

12. The device of claim 1, wherein the one or more circuits are configured and arranged to deliver energy sufficient to ablate the cardiac cells.

13. A device for controlling depolarization in cardiac cells, the device comprising:
   one or more circuits configured and arranged to
      generate an electrical stimulus in a frequency range exceeding 1 kHz and less than 500 kHz; and
      maintain the electrical stimulus over a period of time sufficient to inhibit action potentials in the cardiac cells; and
   an electrode arrangement configured and arranged to
      deliver the electrical stimulus to cardiac cells and depolarize the cardiac cells; and
   wherein the one or more circuits are further configured and arranged to adjust the electrical stimulus relative to artifacts generated at frequencies corresponding to action potentials of the cardiac cells.

14. The device of claim 13, wherein the adjustment to the electrical stimulus includes modifying a pulse shape to reduce onset and offset artifacts.

15. A method for inhibiting excitability of cardiac cells comprising:
   generating a high frequency electrical stimulus in a frequency range exceeding 0.5 kHz and less than 500 kHz;
   delivering the high frequency electrical stimulus to the cardiac cells;
   maintaining the high frequency electrical stimulus to the cardiac cells over a period of time sufficient to inhibit action potentials in the cardiac cells, and during the period of time, simultaneously detecting whether the electrical stimulus has caused inhibition of action potentials in the cardiac cells by monitoring frequency components of an electrical signal coupled to the cardiac tissue while applying the electrical stimulus.

16. The method of claim 15, wherein the high frequency electrical stimulus is between 1 kHz and 10 kHz.

17. The method of claim 15, further including the steps of
   receiving electrical signals from an electrode;
   filtering high frequency components from the electrical signals; and
   detecting, from the filtered electrical signals, electrical action potentials of the cardiac cells.

18. The method of claim 15, wherein the high frequency stimulus stops a re-entry arrhythmia in the cardiac cells.

19. The method of claim 15, further including the steps of detecting whether the high frequency stimulus stops a re-entrant arrhythmia in the cardiac cells, and in response to detecting a stop in the re-entrant arrhythmia, ablating the cardiac cells at a location based on where the high frequency stimulus is delivered.

20. A method for modeling cardiac re-entrant arrhythmia, the method comprising:
   generating a propagating depolarization wave in cardiac tissue by providing an electrical stimulus at a first location in the cardiac tissue; and
   directing the propagation of the depolarization wave back to the first location by inhibiting depolarization of cardiac tissue using high frequency electrical stimulus applied to portions of the cardiac tissue and thereby creating a re-entry arrhythmia.

21. The method of claim 20, further including steps of providing a candidate drug to the cardiac tissue and monitoring the depolarization wave and re-entry arrhythmia.

22. The method of claim 20, wherein the high frequency electrical stimulus is provided at a frequency exceeding 1 kHz and less than 500 kHz.

23. A method for inducing depolarization of cardiac cells, the method comprising:
   generating a high frequency electrical stimulus in a frequency range exceeding 0.5 kHz and less than 500 kHz;
   delivering the high frequency electrical stimulus to the cardiac cells;
   receiving an electrical signal from an electrode;

filtering high frequency components from the electrical signal received from the cardiac cells;

detecting a depolarization event using the filtered electrical signal, by monitoring the filtered electrical signal while delivering the high frequency electrical stimulus to the cardiac cells; and stopping, in response to detecting the depolarization event, the delivery of the high frequency electrical stimulus to the cardiac cells.

24. The method of claim 23, wherein the delivering of the high frequency electrical stimulus is accomplished in vivo, and wherein the step of detecting is performed by one or more circuits filtering, from a measured electrical signal, stimulation-related high frequency components from cardiac tissue-related low frequency components and monitoring for action potentials in the filtered electrical signal.

\* \* \* \* \*